US011528938B2

(12) United States Patent
Twite et al.

(10) Patent No.: US 11,528,938 B2
(45) Date of Patent: *Dec. 20, 2022

(54) NON-NICOTINE POD ASSEMBLIES AND NON-NICOTINE E-VAPING DEVICES

(71) Applicant: Altria Client Services LLC, Richmond, VA (US)

(72) Inventors: Dean Twite, Richmond, VA (US); Yannick Hourmand, Richmond, VA (US); Bipin Patil, Richmond, VA (US); Rangaraj S. Sundar, Richmond, IA (US); Gregory L. Nelson, Chester, VA (US); Niall Gallagher, Richmond, VA (US); Jarrett Keen, Richmond, VA (US); Phillip Diana, Richmond, VA (US); James Yorkshades, Gamlingay (GB)

(73) Assignee: Altria Client Services LLC, Richmond, VA (US)

( * ) Notice: Subject to any disclaimer, the term of this patent is extended or adjusted under 35 U.S.C. 154(b) by 35 days.

This patent is subject to a terminal disclaimer.

(21) Appl. No.: 16/696,081

(22) Filed: Nov. 26, 2019

(65) Prior Publication Data

US 2021/0153568 A1 May 27, 2021

(51) Int. Cl.
A24F 40/42 (2020.01)
A61M 11/04 (2006.01)

(52) U.S. Cl.
CPC ........... A24F 40/42 (2020.01); A61M 11/042 (2014.02)

(58) Field of Classification Search
None
See application file for complete search history.

(56) References Cited

U.S. PATENT DOCUMENTS 5,301,666 A 4/1994 Lerk et al.
6,810,883 B2 11/2004 Felter et al.
(Continued)

FOREIGN PATENT DOCUMENTS

CN 203646511 U 6/2014
CN 203828084 U 9/2014
(Continued)

OTHER PUBLICATIONS

Invitation to Pay Additional Fees for PCT/EP2020/083536 dated Mar. 1, 2021.
(Continued)

Primary Examiner — James Harvey
(74) Attorney, Agent, or Firm — Harness, Dickey & Pierce, P.L.C.

(57) ABSTRACT

A non-nicotine pod assembly for a non-nicotine e-vaping device may include a first section and a second section connected to the first section. The first section may define a pod outlet and be configured to hold a non-nicotine pre-vapor formulation. The second section may define a pod inlet and be configured to heat the non-nicotine pre-vapor formulation. The pod inlet is in fluidic communication with the pod outlet via a flow path. The flow path may include a first diverged portion, a second diverged portion, and a converged portion. A non-nicotine e-vaping device may include a device body defining a through hole configured to receive the non-nicotine pod assembly such that a pod inlet for the air flow is exposed when the non-nicotine pod assembly is seated within the through hole.

21 Claims, 30 Drawing Sheets

(56) References Cited

U.S. PATENT DOCUMENTS

| | | | |
|---|---|---|---|
| D552,232 S | 10/2007 | Collins et al. | |
| 7,350,720 B2 | 4/2008 | Jaworski et al. | |
| 7,987,856 B2 | 8/2011 | Gedevanishvili et al. | |
| 8,291,898 B2 | 10/2012 | Southby et al. | |
| 8,424,540 B2 | 4/2013 | Olegario et al. | |
| 8,733,346 B2 | 5/2014 | Rinker | |
| 9,320,301 B2 | 4/2016 | Memari et al. | |
| 9,532,604 B2 | 1/2017 | Conley et al. | |
| 9,668,523 B2 | 6/2017 | Tucker et al. | |
| 9,750,284 B2 | 9/2017 | Rado | |
| 9,999,258 B2 | 6/2018 | Newcomb et al. | |
| 10,104,913 B2 | 10/2018 | Lau et al. | |
| 11,123,501 B2 | 9/2021 | Nettenstrom | |
| 2009/0241949 A1 | 10/2009 | Smutney et al. | |
| 2012/0199663 A1 | 8/2012 | Qiu | |
| 2014/0123989 A1 | 5/2014 | LaMothe | |
| 2014/0261487 A1 | 9/2014 | Chapman et al. | |
| 2015/0027457 A1 | 1/2015 | Janardhan et al. | |
| 2015/0101625 A1 | 4/2015 | Newton et al. | |
| 2015/0128971 A1 | 5/2015 | Verleur et al. | |
| 2015/0189919 A1 | 7/2015 | Liu | |
| 2015/0208729 A1 | 7/2015 | Monsees et al. | |
| 2015/0342255 A1 | 12/2015 | Wu | |
| 2015/0342258 A1 | 12/2015 | Chen | |
| 2015/0351456 A1 | 12/2015 | Johnson et al. | |
| 2015/0374039 A1 | 12/2015 | Zhu | |
| 2016/0021933 A1 | 1/2016 | Thorens et al. | |
| 2016/0050975 A1 | 2/2016 | Worm et al. | |
| 2016/0120226 A1 | 5/2016 | Rado | |
| 2016/0309787 A1* | 10/2016 | Hawes | A61M 15/06 |
| 2016/0309788 A1 | 10/2016 | Hawes et al. | |
| 2016/0309789 A1 | 10/2016 | Thomas, Jr. | |
| 2016/0324216 A1 | 11/2016 | Li et al. | |
| 2016/0345626 A1 | 12/2016 | Wong et al. | |
| 2016/0360789 A1* | 12/2016 | Hawes | H05B 1/0297 |
| 2016/0374399 A1 | 12/2016 | Monsees et al. | |
| 2017/0027227 A1 | 2/2017 | Lipowicz | |
| 2017/0035115 A1 | 2/2017 | Monsees et al. | |
| 2017/0042246 A1* | 2/2017 | Lau | H05B 1/0297 |
| 2017/0071249 A1 | 3/2017 | Ampolini et al. | |
| 2017/0071253 A1 | 3/2017 | Revell | |
| 2017/0095624 A1 | 4/2017 | Davidson et al. | |
| 2017/0135409 A1 | 5/2017 | Cameron | |
| 2017/0150753 A1 | 6/2017 | Macko | |
| 2017/0172209 A1 | 6/2017 | Saydar et al. | |
| 2017/0197044 A1 | 7/2017 | Buchberger | |
| 2017/0202265 A1 | 7/2017 | Hawes et al. | |
| 2017/0231281 A1 | 8/2017 | Hatton et al. | |
| 2017/0231282 A1 | 8/2017 | Bowen et al. | |
| 2017/0258134 A1 | 9/2017 | Kane | |
| 2018/0027879 A1 | 2/2018 | Gavrielov et al. | |
| 2018/0104214 A1 | 4/2018 | Raichman | |
| 2019/0099562 A1 | 4/2019 | Nettenstrom et al. | |
| 2019/0104763 A1 | 4/2019 | Tucker et al. | |
| 2019/0104764 A1 | 4/2019 | Tucker et al. | |
| 2019/0142071 A1 | 5/2019 | Seok | |
| 2019/0166913 A1* | 6/2019 | Trzecieski | A24F 40/42 |
| 2019/0208820 A1 | 7/2019 | Reevell | |
| 2019/0254345 A1 | 8/2019 | Hepworth et al. | |
| 2019/0274362 A1* | 9/2019 | Newcomb | H05B 1/0227 |
| 2019/0335813 A1 | 11/2019 | Qiu | |
| 2020/0114095 A1* | 4/2020 | Holroyd | A61M 15/0036 |
| 2020/0376210 A1 | 12/2020 | Simpson et al. | |
| 2020/0397046 A1 | 12/2020 | Lin et al. | |
| 2021/0068458 A1 | 3/2021 | Lomas et al. | |
| 2021/0153548 A1 | 5/2021 | Twite et al. | |
| 2021/0153549 A1* | 5/2021 | Twite | A24F 40/485 |
| 2021/0153566 A1 | 5/2021 | Hourmand et al. | |
| 2021/0153567 A1 | 5/2021 | Twite et al. | |
| 2021/0153568 A1 | 5/2021 | Twite et al. | |
| 2021/0153569 A1 | 5/2021 | Twite et al. | |
| 2021/0268215 A1 | 9/2021 | Israel et al. | |
| 2022/0142257 A1 | 5/2022 | Austin et al. | |

FOREIGN PATENT DOCUMENTS

| | | |
|---|---|---|
| CN | 108741232 A | 11/2018 |
| CN | 208692313 U | 4/2019 |
| EP | 3560360 A1 | 10/2019 |
| EP | 3569073 A1 | 11/2019 |
| WO | WO-2016/079152 A1 | 5/2016 |
| WO | WO-2016/096780 A1 | 6/2016 |
| WO | WO-2016/172023 A1 | 10/2016 |
| WO | WO-2016/172802 A1 | 11/2016 |
| WO | WO-2017/102969 A1 | 6/2017 |
| WO | WO-2017/153597 A1 | 9/2017 |
| WO | WO-2017/163045 A1 | 9/2017 |
| WO | WO-2017/163052 A1 | 9/2017 |
| WO | WO-2017/207443 A1 | 12/2017 |
| WO | WO-2018/125674 A1 | 7/2018 |
| WO | WO-2018217440 A1 | 11/2018 |
| WO | WO-2020/039177 A1 | 2/2020 |
| WO | WO-2020/039179 A1 | 2/2020 |

OTHER PUBLICATIONS

Invitation to Pay Additional Fees for PCT/EP2020/083539 dated Mar. 2, 2021.
Invitation to Pay Additional Fees for PCT/EP2020/083551 dated Mar. 2, 2021.
Invitation to Pay Additional Fees for PCT/EP2020/083549 dated Mar. 2, 2021.
International Search Report and Written Opinion for PCT/US2020/045590 dated Dec. 14, 2020.
International Search Report and Written Opinion for PCT/US2020/045691 dated Jan. 12, 2021.
International Search Report and Written Opinion for corresponding International application No. PCT/EP2020/083536 dated Jun. 11, 2021.
International Search Report and Written Opinion for corresponding International application No. PCT/EP2020/083549 dated Jun. 11, 2021.
International Search Report and Written Opinion for corresponding International application No. PCT/EP2020/083539 dated Jun. 11, 2021.
Office Action for U.S. Appl. No. 16/695,643 dated Sep. 1, 2021.
Office Action for U.S. Appl. No. 16/695,692 dated Sep. 22, 2021.
International Search Report and Written Opinion for corresponding International application No. PCT/EP2020/083551 dated Jun. 11, 2021.
International Search Report and Written Opinion for PCT/US2020/045692 dated Nov. 12, 2020.
International Search Report and Written Opinion for PCT/US2020/045588 dated Feb. 2, 2021.
Invitation to Pay Fees for PCT/EP2020/083551 dated Oct. 14, 2021.
Office Action for U.S. Appl. No. 16/695,515 dated Jul. 28, 2021.
Office Action for U.S. Appl. No. 16/696,189 dated Oct. 14, 2021.
Written Opinion for PCT/EP2020/083549 dated Oct. 15, 2021.
Written Opinion for PCT/EP2020/083536 dated Oct. 12, 2021.
Written Opinion for PCT/EP2020/083539 dated Oct. 14, 2021.
Notice of Allowance for U.S. Appl. No. 16/696,007 dated Jan. 28, 2022.
Notice of Allowance for U.S. Appl. No. 16/695,515 dated Feb. 1, 2022.
Office Action for U.S. Appl. No. 16/696,007 dated Nov. 3, 2021.
Office Action for U.S. Appl. No. 16/696,189 dated Jan. 10, 2022.
Notice of Allowance for U.S. Appl. No. 16/695,643 dated Dec. 20, 2021.
Notice of Allowance for U.S. Appl. No. 16/695,692 dated Jan. 4, 2022.
Written Opinion for corresponding International application No. PCT/EP2020/083551 dated Nov. 19, 2021.
Notice of Allowance for U.S. Appl. No. 16/696,007 dated Mar. 7, 2022.
Notice of Allowance for U.S. Appl. No. 16/696,189 dated Mar. 10, 2022.

(56) References Cited

OTHER PUBLICATIONS

Notice of Allowance for U.S. Appl. No. 16/695,692 dated Mar. 21, 2022.
International Preliminary Report on Patentability for PCT/EP2020/083536 dated Feb. 23, 2022.
Notice of Allowance for U.S. Appl. No. 16/695,643 dated Mar. 24, 2022.
Office Action for U.S. Appl. No. 16/695,643 dated Apr. 22, 2022.
Notice of Allowance for U.S. Appl. No. 16/695,692 dated Apr. 25, 2022.
Notice of Allowance for U.S. Appl. No. 16/696,189 dated Mar. 28, 2022.
International Preliminary Report on Patentability for PCT/EP2020/083539 dated Feb. 24, 2022.
International Preliminary Report on Patentability for PCT/EP2020/083551 dated Feb. 24, 2022.
International Preliminary Report on Patentability for PCT/EP2020/083549 dated Feb. 24, 2022.
Office Action for U.S. Appl. No. 16/695,415 dated Mar. 29, 2022.
Office Action for U.S. Appl. No. 16/695,563 dated Mar. 30, 2022.
Notice of Allowance for U.S. Appl. No. 16/696,007 dated Apr. 28, 2022.
Notice of Allowance for U.S. Appl. No. 16/696,189 dated May 5, 2022.
Notice of Allowance for corresponding U.S. Appl. No. 16/695,692 dated Jul. 13, 2022.
Notice of Allowance for U.S. Appl. No. 16/696,007 dated Jul. 18, 2022.
Office Action for U.S. Appl. No. 16/695,515 dated May 27, 2022.
International Preliminary Report on Patentability for PCT/US2020/045590 dated Jun. 9, 2022.
International Preliminary Report on Patentability for PCT/US2020/045692 dated Jun. 9, 2022.
International Preliminary Report on Patentability for PCT/US2020/045588 dated Jun. 9, 2022.
International Preliminary Report on Patentability for PCT/US2020/045691 dated Jun. 9, 2022.
Notice of Allowance for U.S. Appl. No. 16/695,415 dated Jul. 25, 2022.
Notice of Allowance for U.S. Appl. No. 16/695,563 dated Jul. 22, 2022.
Notice of Allowance for U.S. Appl. No. 16/696,189 dated Jul. 27, 2022.
Notice of Allowance dated Oct. 25, 2022 issued in corresponding U.S. Appl. No. 16/695,643.

* cited by examiner

NON-NICOTINE POD ASSEMBLIES AND NON-NICOTINE E-VAPING DEVICES

BACKGROUND

Field

The present disclosure relates to non-nicotine electronic vaping (e-vaping) devices.

Description of Related Art

Some non-nicotine e-vaping devices include a first section coupled to a second section. The first section may include a wick and a heater. The wick is configured to move a non-nicotine pre-vapor formulation via capillary action and is positioned so as to extend into a reservoir and a vapor passage. The heater is in thermal contact with the wick and is configured to vaporize the non-nicotine pre-vapor formulation drawn via the wick into the vapor passage. The second section includes a power source configured to supply an electric current to the heater during vaping. The initiation of the operation of the non-nicotine e-vaping device may be achieved through manual- and/or puff-activation.

SUMMARY

At least one embodiment relates to a non-nicotine pod assembly for a non-nicotine e-vaping device.

In an example embodiment, a non-nicotine pod assembly may include a first section and a second section connected to the first section. The first section may define a pod outlet and be configured to hold a non-nicotine pre-vapor formulation. The second section may define a pod inlet and be configured to heat the non-nicotine pre-vapor formulation. The pod inlet is in fluidic communication with the pod outlet via a flow path. The flow path may include a first diverged portion, a second diverged portion, and a converged portion.

At least one embodiment relates to a device body for a non-nicotine e-vaping device.

In an example embodiment, a device body may include a device housing defining a through hole configured to receive a non-nicotine pod assembly. The through hole includes an upstream sidewall and a downstream sidewall. The upstream sidewall includes at least one upstream protrusion, and the downstream sidewall includes at least one downstream protrusion. The at least one downstream protrusion is retractable relative to adjacent surfaces of the downstream sidewall and is configured to engage with at least one downstream recess of the non-nicotine pod assembly to retain the non-nicotine pod assembly within the through hole.

At least one embodiment relates to a non-nicotine e-vaping device.

In an example embodiment, a non-nicotine e-vaping device may include a non-nicotine pod assembly and a device body configured to receive the non-nicotine pod assembly. The non-nicotine pod assembly may include a first section and a second section. The first section may be configured to hold a non-nicotine pre-vapor formulation. The second section may be configured to diverge and converge an air flow into the non-nicotine pod assembly prior to a passage of the air flow through the first section. The device body may define a through hole configured to receive the non-nicotine pod assembly such that a pod inlet for the air flow is exposed when the non-nicotine pod assembly is seated within the through hole.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
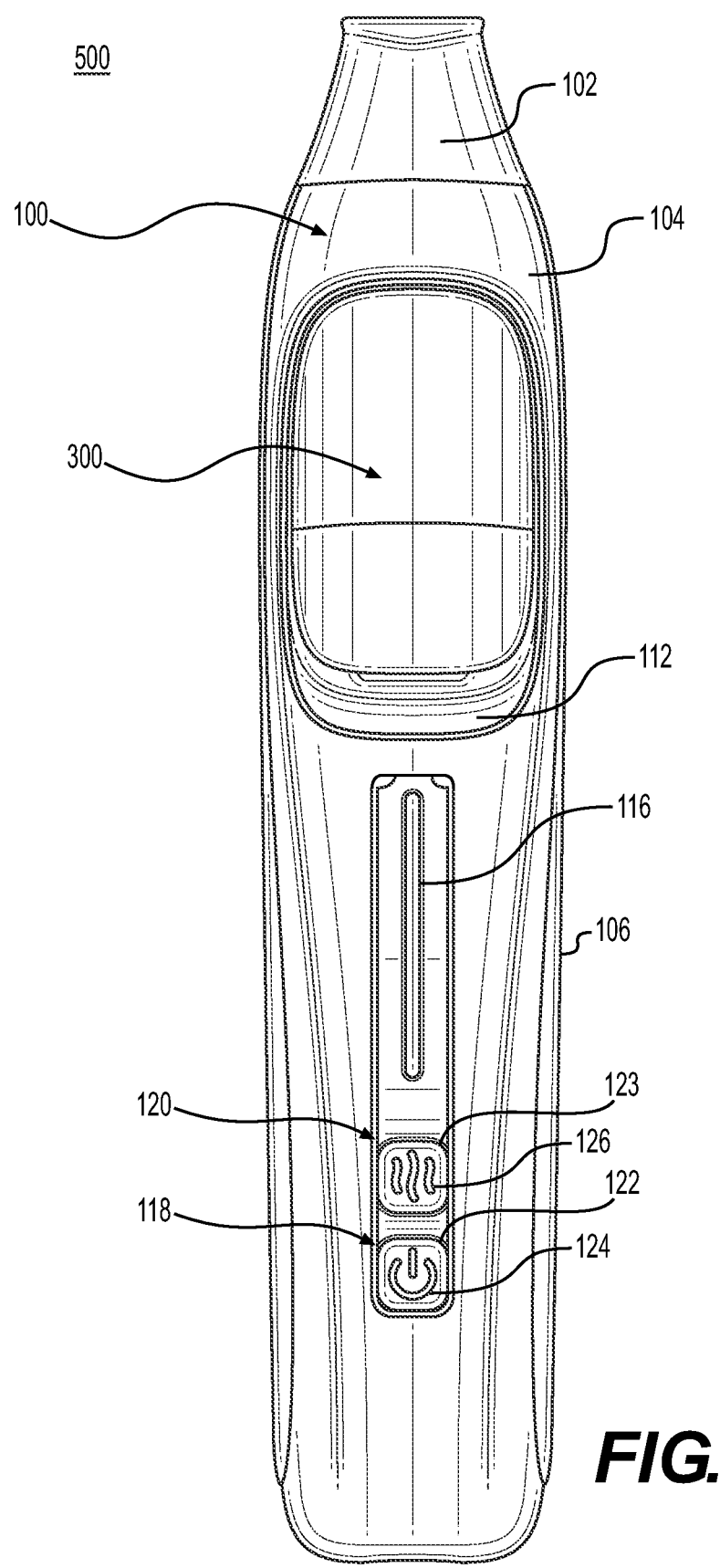
FIG. 1 is a front view of a non-nicotine e-vaping device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," "covering," etc. another element or layer, it may be directly on, connected to, coupled to, attached to, adjacent to, covering, etc. the other element or layer or intervening elements or layers may be present. In contrast, when an element is referred to as being "directly on," "directly connected to," "directly coupled to," etc. another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the term "same" or "identical" is used in the description of example embodiments, it should be understood that some imprecisions may exist. Thus, when one element or value is referred to as being the same as another element or value, it should be understood that the element or value is the same as the other element or value within a manufacturing or operational tolerance range (e.g., ±10%).

When the terms "about" or "substantially" are used in connection with a numerical value, it should be understood that the associated numerical value includes a manufacturing or operational tolerance (e.g., ±10%) around the stated numerical value. Moreover, when the words "generally" and "substantially" are used in connection with a geometric shape, it should be understood that the precision of the geometric shape is not required but that latitude for the shape is within the scope of the disclosure.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 2:
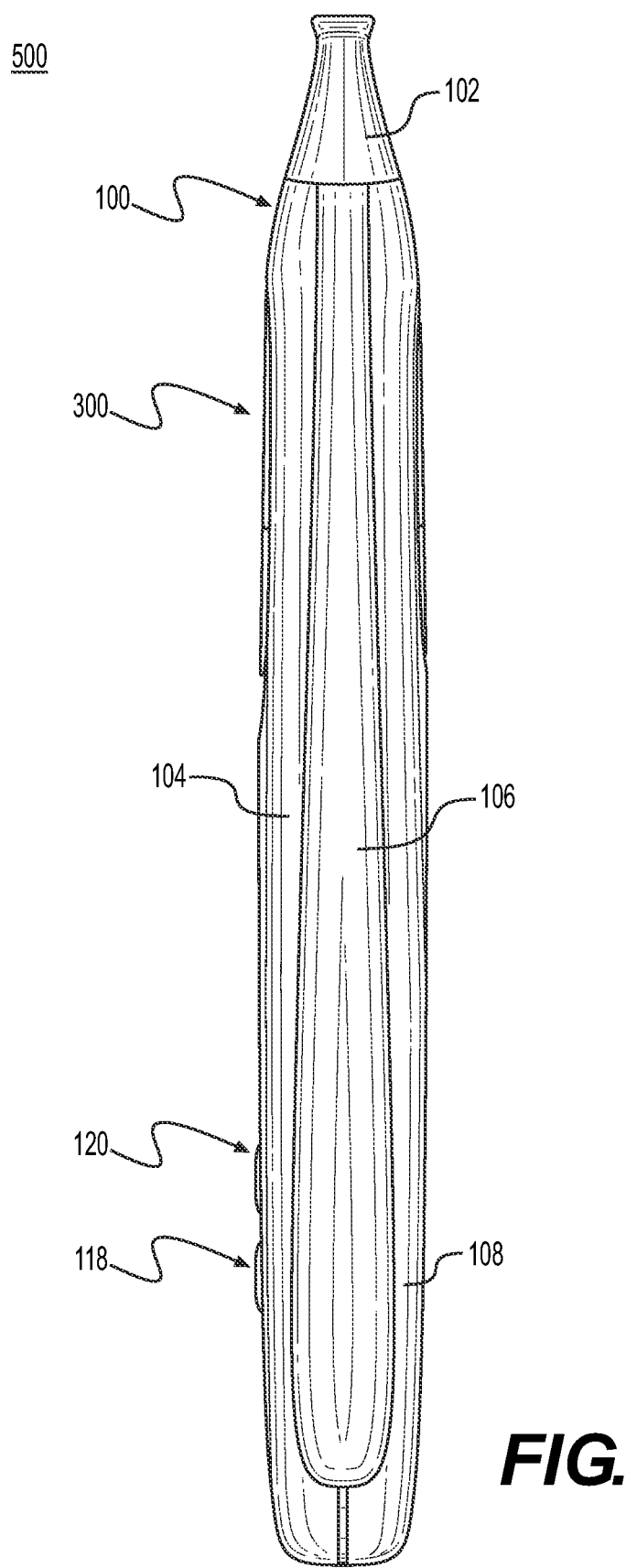
FIG. 2 is a side view of the non-nicotine e-vaping device of FIG. 1.
Figure 3:
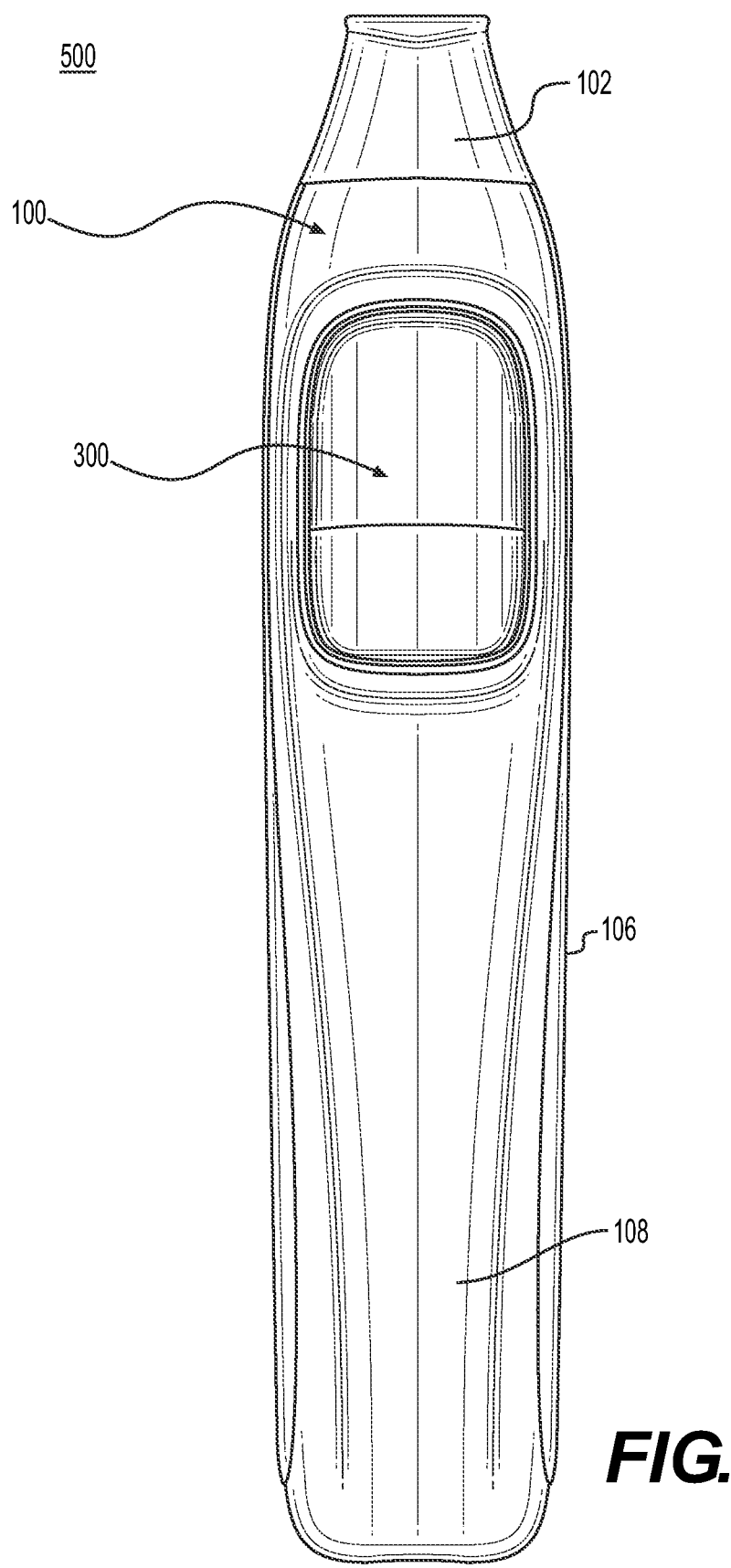
FIG. 3 is a rear view of the non-nicotine e-vaping device of FIG. 1.

FIG. 1 is a front view of a non-nicotine e-vaping device according to an example embodiment. FIG. 2 is a side view of the non-nicotine e-vaping device of FIG. 1. FIG. 3 is a rear view of the non-nicotine e-vaping device of FIG. 1. Referring to FIGS. 1-3, a non-nicotine e-vaping device 500 includes a device body 100 that is configured to receive a non-nicotine pod assembly 300. The non-nicotine pod assembly 300 is a modular article configured to hold a non-nicotine pre-vapor formulation. A non-nicotine pre-vapor formulation is a material or combination of materials that is devoid of nicotine and that may be transformed into a non-nicotine vapor. For example, the non-nicotine pre-vapor formulation may include a liquid, solid, and/or gel formulation. These may include, for example and without limitation, solutions and suspensions (e.g., emulsions) containing water, oil, beads, solvents, active ingredients, ethanol, plant extracts, non-nicotine compounds, natural or artificial flavors, vapor formers such as glycerin and propylene glycol, and/or any other ingredients that may be suitable for vaping. During vaping, the non-nicotine e-vaping device 500 is configured to heat the non-nicotine pre-vapor formulation to generate a non-nicotine vapor. Non-nicotine vapor, non-nicotine aerosol, and non-nicotine dispersion are used interchangeably and refer to the matter generated or outputted by the devices disclosed, claimed, and/or equivalents thereof, wherein such matter is devoid of nicotine.

As shown in FIGS. 1 and 3, the non-nicotine e-vaping device 500 extends in a longitudinal direction and has a length that is greater than its width. In addition, as shown in FIG. 2, the length of the non-nicotine e-vaping device 500 is also greater than its thickness. Furthermore, the width of the non-nicotine e-vaping device 500 may be greater than its thickness. Assuming an x-y-z Cartesian coordinate system, the length of the non-nicotine e-vaping device 500 may be measured in the y-direction, the width may be measured in the x-direction, and the thickness may be measured in the z-direction. The non-nicotine e-vaping device 500 may have a substantially linear form with tapered ends based on its front, side, and rear views, although example embodiments are not limited thereto.

The device body 100 includes a front cover 104, a frame 106, and a rear cover 108. The front cover 104, the frame 106, and the rear cover 108 form a device housing that encloses mechanical components, electronic components, and/or circuitry associated with the operation of the non-nicotine e-vaping device 500. For instance, the device housing of the device body 100 may enclose a power source configured to power the non-nicotine e-vaping device 500, which may include supplying an electric current to the non-nicotine pod assembly 300. In addition, when assembled, the front cover 104, the frame 106, and the rear cover 108 may constitute a majority of the visible portion of the device body 100. The device housing may be regarded as including all constituent parts of the device body 100 except for the mouthpiece 102. Stated differently, the mouthpiece 102 and the device housing may be regarded as forming the device body 100.

The front cover 104 (e.g., first cover) defines a primary opening configured to accommodate a bezel structure 112. The primary opening may have a rounded rectangular shape, although other shapes are possible depending on the shape of the bezel structure 112. The bezel structure 112 defines a through hole 150 configured to receive the non-nicotine pod assembly 300. The through hole 150 is discussed herein in more detail in connection with, for instance, FIG. 9.

The front cover 104 also defines a secondary opening configured to accommodate a light guide arrangement. The secondary opening may resemble a slot (e.g., segmented slot), although other shapes are possible depending on the shape of the light guide arrangement. In an example embodiment, the light guide arrangement includes a light guide lens 116. Furthermore, the front cover 104 defines a tertiary opening and a quaternary opening configured to accommodate a first button 118 and a second button 120. Each of the tertiary opening and the quaternary opening may resemble a rounded square, although other shapes are possible depending on the shapes of the buttons. A first button housing 122 is configured to expose a first button lens 124, while a second button housing 123 is configured to expose a second button lens 126.

The operation of the non-nicotine e-vaping device 500 may be controlled by the first button 118 and the second button 120. For instance, the first button 118 may be a power button, and the second button 120 may be an intensity button. Although two buttons are shown in the drawings, it should be understood that more (or less) buttons may be provided depending on the available features and desired user interface.

The frame 106 (e.g., base frame) is the central support structure for the device body 100 (and the non-nicotine e-vaping device 500 as a whole). The frame 106 may be referred to as a chassis. The frame 106 includes a proximal end, a distal end, and a pair of side sections between the proximal end and the distal end. The proximal end and the distal end may also be referred to as the downstream end and the upstream end, respectively. As used herein, "proximal" (and, conversely, "distal") is in relation to an adult vaper during vaping, and "downstream" (and, conversely, "upstream") is in relation to a flow of the non-nicotine vapor. A bridging section may be provided between the opposing inner surfaces of the side sections (e.g., about midway along the length of the frame 106) for additional strength and stability. The frame 106 may be integrally formed so as to be a monolithic structure.

With regard to material of construction, the frame 106 may be formed of an alloy or a plastic. The alloy (e.g., die cast grade, machinable grade) may be an aluminum (Al) alloy or a zinc (Zn) alloy. The plastic may be a polycarbonate (PC), an acrylonitrile butadiene styrene (ABS), or a combination thereof (PC/ABS). For instance, the polycarbonate may be LUPOY SC1004A. Furthermore, the frame 106 may be provided with a surface finish for functional and/or aesthetic reasons (e.g., to provide a premium appearance). In an example embodiment, the frame 106 (e.g., when formed of an aluminum alloy) may be anodized. In another embodiment, the frame 106 (e.g., when formed of a zinc alloy) may be coated with a hard enamel or painted. In another embodiment, the frame 106 (e.g., when formed of a polycarbonate) may be metallized. In yet another embodiment, the frame 106 (e.g., when formed of an acrylonitrile butadiene styrene) may be electroplated. It should be understood that the materials of construction with regard to the frame 106 may also be applicable to the front cover 104, the rear cover 108, and/or other appropriate parts of the non-nicotine e-vaping device 500.

The rear cover 108 (e.g., second cover) also defines an opening configured to accommodate the bezel structure 112. The opening may have a rounded rectangular shape, although other shapes are possible depending on the shape of the bezel structure 112. In an example embodiment, the opening in the rear cover 108 is smaller than the primary opening in the front cover 104. In addition, although not shown, it should be understood that a light guide arrangement and/or buttons may be provided on the rear of the non-nicotine e-vaping device 500 in addition to (or in lieu of) the light guide arrangement and buttons on the front of the non-nicotine e-vaping device 500.

The front cover 104 and the rear cover 108 may be configured to engage with the frame 106 via a snap-fit arrangement. For instance, the front cover 104 and/or the rear cover 108 may include clips configured to interlock with corresponding mating members of the frame 106. In a non-limiting embodiment, the clips may be in a form of tabs with orifices configured to receive the corresponding mating members (e.g., protrusions with beveled edges) of the frame 106. Alternatively, the front cover 104 and/or the rear cover 108 may be configured to engage with the frame 106 via an interference fit (which may also be referred to as a press fit or friction fit). However, it should be understood that the front cover 104, the frame 106, and the rear cover 108 may be coupled via other suitable arrangements and techniques.

The device body 100 also includes a mouthpiece 102. The mouthpiece 102 may be secured to the proximal end of the frame 106. Additionally, as shown in FIG. 2, in an example embodiment where the frame 106 is sandwiched between the front cover 104 and the rear cover 108, the mouthpiece 102 may abut the front cover 104, the frame 106, and the rear cover 108. Furthermore, in a non-limiting embodiment, the mouthpiece 102 may be joined with the device housing via a bayonet connection.

Figure 4:
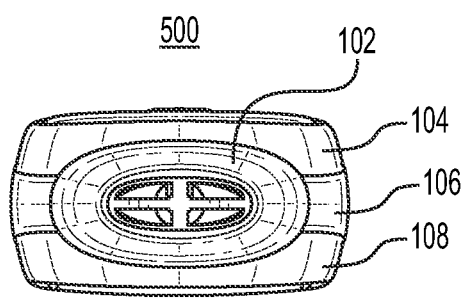
FIG. 4 is a proximal end view of the non-nicotine e-vaping device of FIG. 1.

FIG. 4 is a proximal end view of the non-nicotine e-vaping device of FIG. 1. Referring to FIG. 4, the outlet face of the mouthpiece 102 defines a plurality of vapor outlets. In a non-limiting embodiment, the outlet face of the mouthpiece 102 may be elliptically-shaped. In addition, the outlet face of the mouthpiece 102 may include a first crossbar corresponding to a major axis of the elliptically-shaped outlet face and a second crossbar corresponding to a minor axis of the elliptically-shaped outlet face. Furthermore, the first crossbar and the second crossbar may intersect perpendicularly and be integrally formed parts of the mouthpiece 102. Although the outlet face is shown as defining four vapor outlets, it should be understood that example embodiments are not limited thereto. For instance, the outlet face may define less than four (e.g., one, two) vapor outlets or more than four (e.g., six, eight) vapor outlets.

Figure 5:
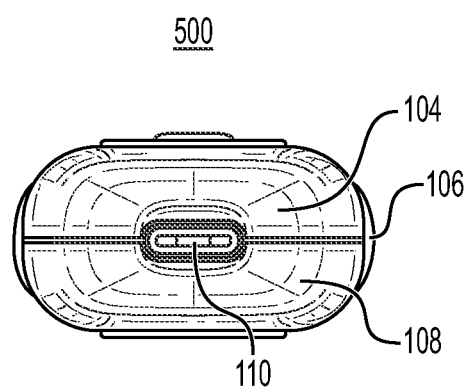
FIG. 5 is a distal end view of the non-nicotine e-vaping device of FIG. 1.

FIG. 5 is a distal end view of the non-nicotine e-vaping device of FIG. 1. Referring to FIG. 5, the distal end of the non-nicotine e-vaping device 500 includes a port 110. The port 110 is configured to receive an electric current (e.g., via a USB/mini-USB cable) from an external power source so as to charge an internal power source within the non-nicotine e-vaping device 500. In addition, the port 110 may also be configured to send data to and/or receive data (e.g., via a USB/mini-USB cable) from another non-nicotine e-vaping device or other electronic device (e.g., phone, tablet, computer). Furthermore, the non-nicotine e-vaping device 500 may be configured for wireless communication with another electronic device, such as a phone, via an application software (app) installed on that electronic device. In such an instance, an adult vaper may control or otherwise interface with the non-nicotine e-vaping device 500 (e.g., locate the non-nicotine e-vaping device, check usage information, change operating parameters) through the app.

Figure 6:
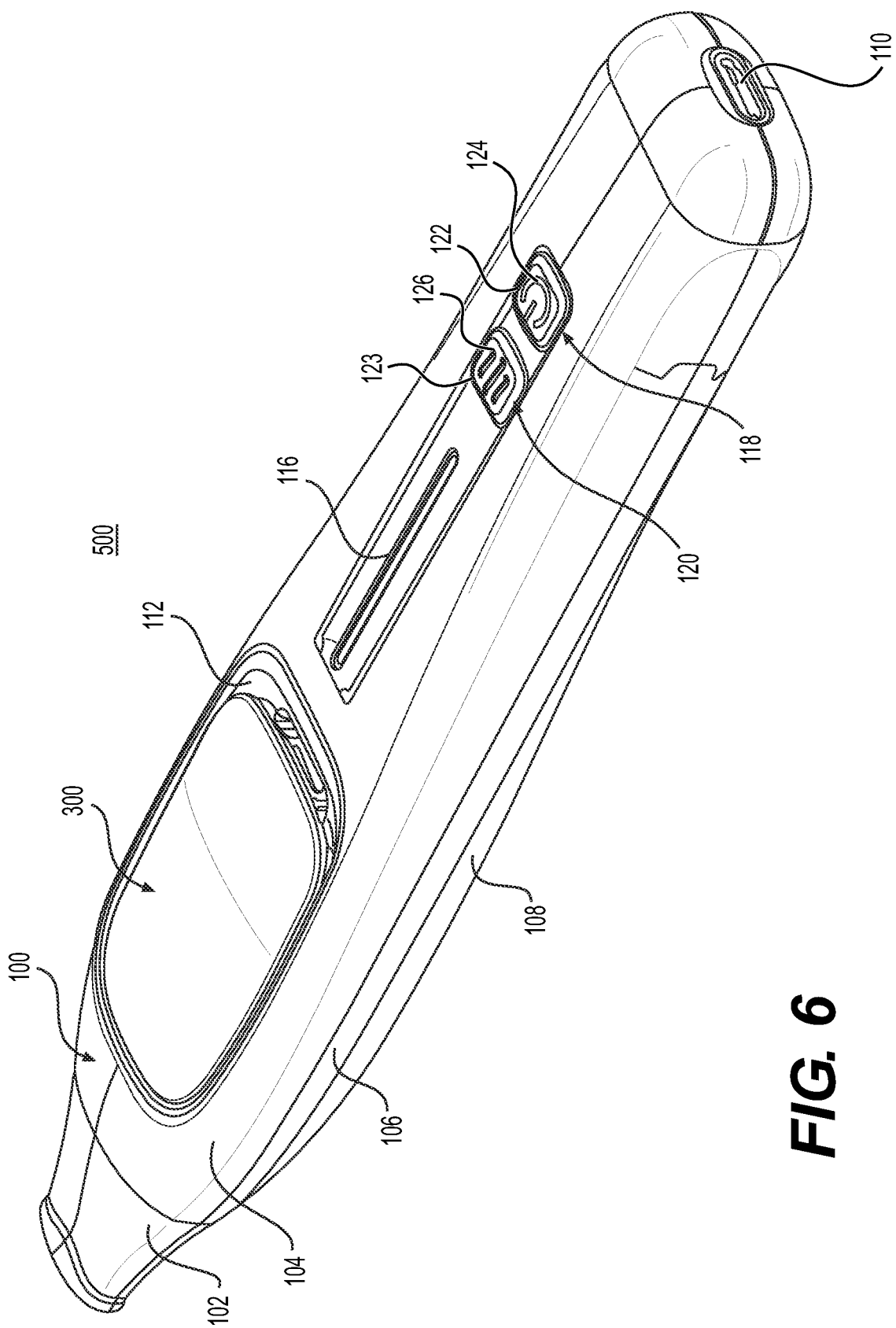
FIG. 6 is a perspective view of the non-nicotine e-vaping device of FIG. 1.
Figure 7:
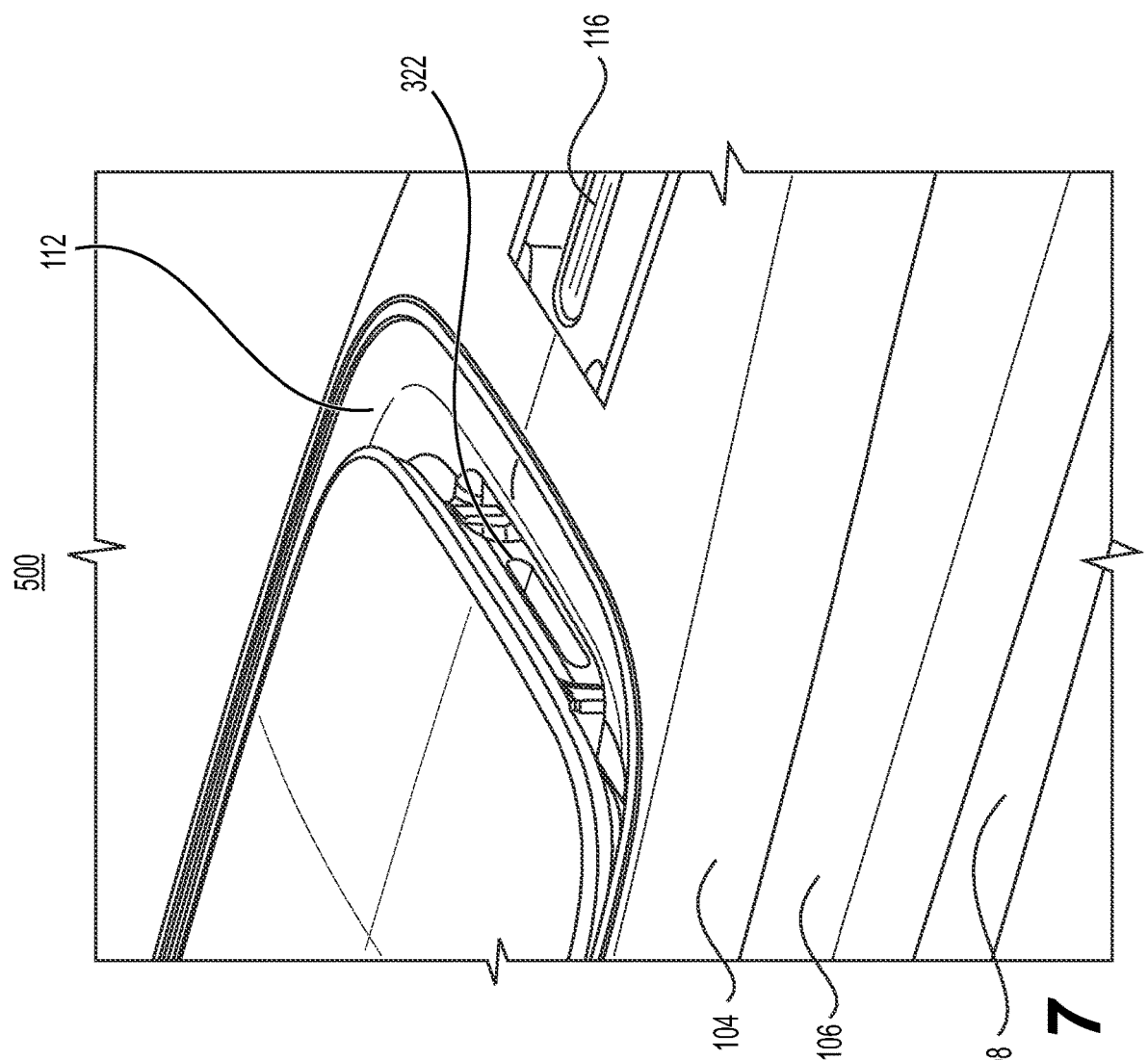
FIG. 7 is an enlarged view of the pod inlet in FIG. 6.

FIG. 6 is a perspective view of the non-nicotine e-vaping device of FIG. 1. FIG. 7 is an enlarged view of the pod inlet in FIG. 6. Referring to FIGS. 6-7, and as briefly noted above, the non-nicotine e-vaping device 500 includes a non-nicotine pod assembly 300 configured to hold a non-nicotine pre-vapor formulation. The non-nicotine pod assembly 300 has an upstream end (which faces the light guide arrangement) and a downstream end (which faces the mouthpiece 102). In a non-limiting embodiment, the upstream end is an opposing surface of the non-nicotine pod assembly 300 from the downstream end. The upstream end of the non-nicotine pod assembly 300 defines a pod inlet 322. The device body 100 defines a through hole (e.g., through hole 150 in FIG. 9) configured to receive the non-nicotine pod assembly 300. In an example embodiment, the bezel structure 112 of the device body 100 defines the through hole and includes an upstream rim. As shown, particularly in FIG. 7, the upstream rim of the bezel structure 112 is angled (e.g., dips inward) so as to expose the pod inlet 322 when the non-nicotine pod assembly 300 is seated within the through hole of the device body 100.

For instance, rather than following the contour of the front cover 104 (so as to be relatively flush with the front face of the non-nicotine pod assembly 300 and, thus, obscure the pod inlet 322), the upstream rim of the bezel structure 112 is in a form of a scoop configured to direct ambient air into the pod inlet 322. This angled/scoop configuration (e.g., which may be curved) may help reduce or prevent the blockage of the air inlet (e.g., pod inlet 322) of the non-nicotine e-vaping device 500. The depth of the scoop may be such that less than half (e.g., less than a quarter) of the upstream end face of the non-nicotine pod assembly 300 is exposed. Additionally, in a non-limiting embodiment, the pod inlet 322 is in a form of a slot. Furthermore, if the device body 100 is regarded as extending in a first direction, then the slot may be regarded as extending in a second direction, wherein the second direction is transverse to the first direction.

Figure 8:
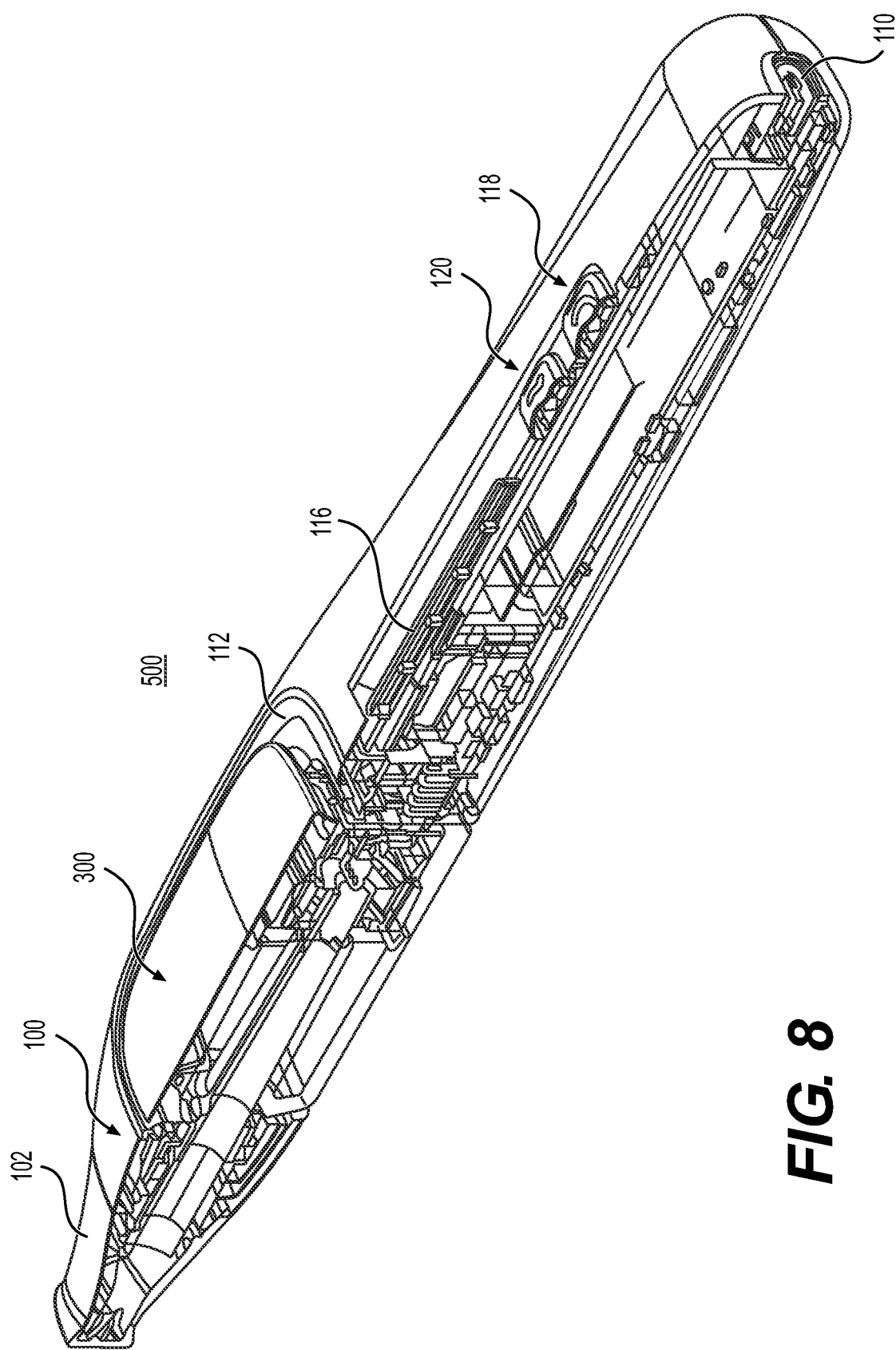
FIG. 8 is a cross-sectional view of the non-nicotine e-vaping device of FIG. 6.

FIG. 8 is a cross-sectional view of the non-nicotine e-vaping device of FIG. 6. In FIG. 8, the cross-section is taken along the longitudinal axis of the non-nicotine e-vaping device 500. As shown, the device body 100 and the non-nicotine pod assembly 300 include mechanical components, electronic components, and/or circuitry associated with the operation of the non-nicotine e-vaping device 500, which are discussed in more detail herein and/or are incorporated by reference herein. For instance, the non-nicotine pod assembly 300 may include mechanical components configured to actuate to release the non-nicotine pre-vapor formulation from a sealed reservoir within. The non-nicotine pod assembly 300 may also have mechanical aspects configured to engage with the device body 100 to facilitate the insertion and seating of the non-nicotine pod assembly 300.

Additionally, the non-nicotine pod assembly 300 may be a "smart pod" that includes electronic components and/or circuitry configured to store, receive, and/or transmit information to/from the device body 100. Such information may be used to authenticate the non-nicotine pod assembly 300 for use with the device body 100 (e.g., to prevent usage of an unapproved/counterfeit non-nicotine pod assembly). Furthermore, the information may be used to identify a type of the non-nicotine pod assembly 300 which is then correlated with a vaping profile based on the identified type. The vaping profile may be designed to set forth the general parameters for the heating of the non-nicotine pre-vapor formulation and may be subject to tuning, refining, or other adjustment by an adult vaper before and/or during vaping.

The non-nicotine pod assembly 300 may also communicate other information with the device body 100 that may be relevant to the operation of the non-nicotine e-vaping device 500. Examples of relevant information may include a level of the non-nicotine pre-vapor formulation within the non-nicotine pod assembly 300 and/or a length of time that has passed since the non-nicotine pod assembly 300 was inserted into the device body 100 and activated. For instance, if the non-nicotine pod assembly 300 was inserted into the device body 100 and activated more than a certain period of time prior (e.g., more than 6 months ago), the non-nicotine e-vaping device 500 may not permit vaping, and the adult vaper may be prompted to change to a new non-nicotine pod assembly even though the non-nicotine pod assembly 300 still contains adequate levels of non-nicotine pre-vapor formulation.

The device body 100 may include mechanical components (e.g. complementary structures) configured to engage, hold, and/or activate the non-nicotine pod assembly 300. In addition, the device body 100 may include electronic components and/or circuitry configured to receive an electric current to charge an internal power source (e.g., battery) which, in turn, is configured to supply power to the non-nicotine pod assembly 300 during vaping. Furthermore, the device body 100 may include electronic components and/or circuitry configured to communicate with the non-nicotine pod assembly 300, a different non-nicotine e-vaping device, other electronic devices (e.g., phone, tablet, computer), and/or the adult vaper. The information being communicated may include pod-specific data, current vaping details, and/or past vaping patterns/history. The adult vaper may be notified of such communications with feedback that is haptic (e.g., vibrations), auditory (e.g., beeps), and/or visual (e.g., colored/blinking lights). The charging and/or communication of information may be performed with the port 110 (e.g., via a USB/mini-USB cable).

Figure 9:
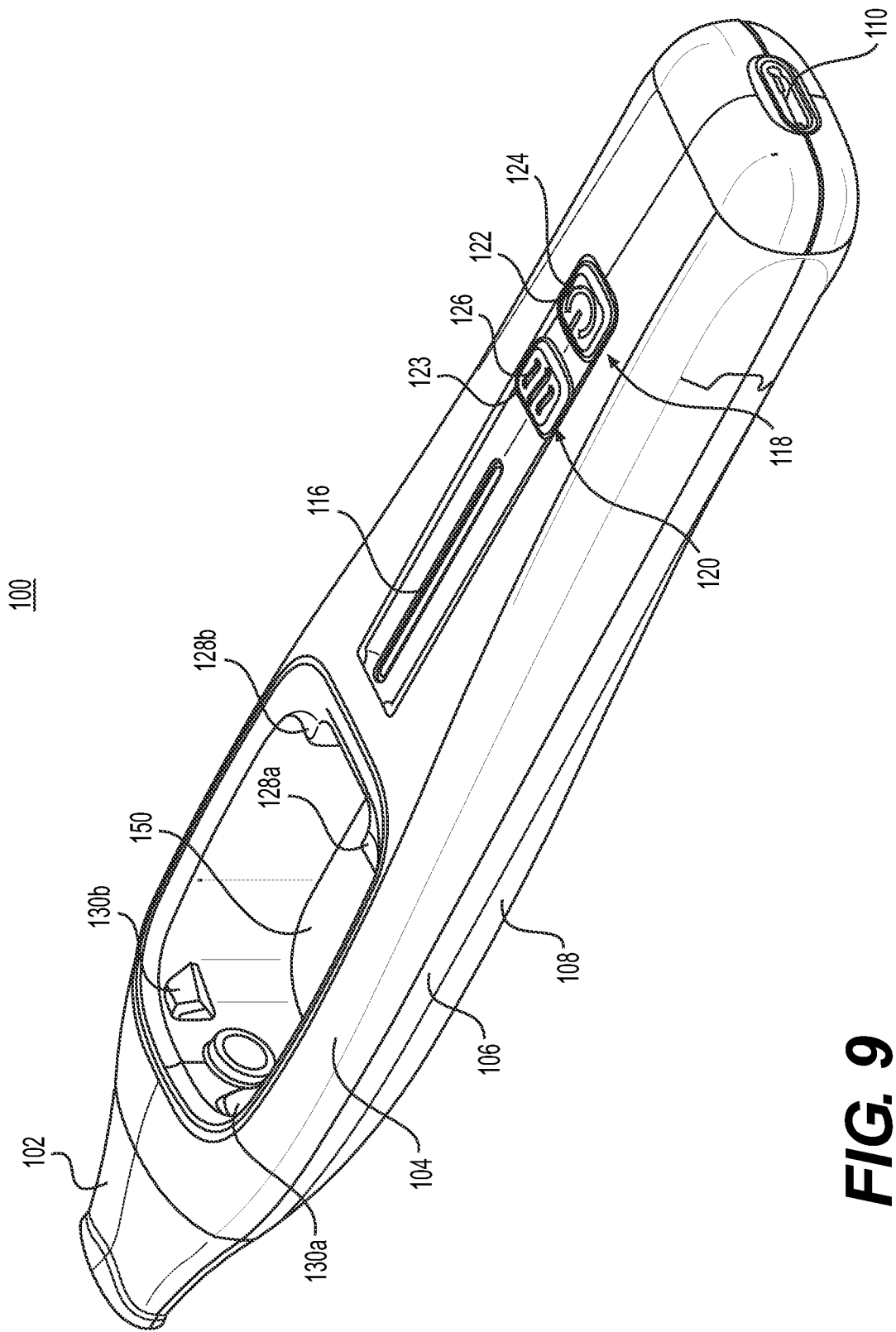
FIG. 9 is a perspective view of the device body of the non-nicotine e-vaping device of FIG. 6.

FIG. 9 is a perspective view of the device body of the non-nicotine e-vaping device of FIG. 6. Referring to FIG. 9, the bezel structure 112 of the device body 100 defines a through hole 150. The through hole 150 is configured to receive a non-nicotine pod assembly 300. To facilitate the insertion and seating of the non-nicotine pod assembly 300 within the through hole 150, the upstream rim of the bezel structure 112 includes a first upstream protrusion 128a and a second upstream protrusion 128b. The through hole 150 may have a rectangular shape with rounded corners. In an example embodiment, the first upstream protrusion 128a and the second upstream protrusion 128b are integrally formed with the bezel structure 112 and located at the two rounded corners of the upstream rim.

The downstream sidewall of the bezel structure 112 may define a first downstream opening, a second downstream opening, and a third downstream opening. A retention structure including a first downstream protrusion 130a and a second downstream protrusion 130b is engaged with the bezel structure 112 such that the first downstream protrusion 130a and the second downstream protrusion 130b protrude through the first downstream opening and the second downstream opening, respectively, of the bezel structure 112 and into the through hole 150. In addition, a distal end of the mouthpiece 102 extends through the third downstream opening of the bezel structure 112 and into the through hole 150 so as to be between the first downstream protrusion 130a and the second downstream protrusion 130b.

Figure 10:
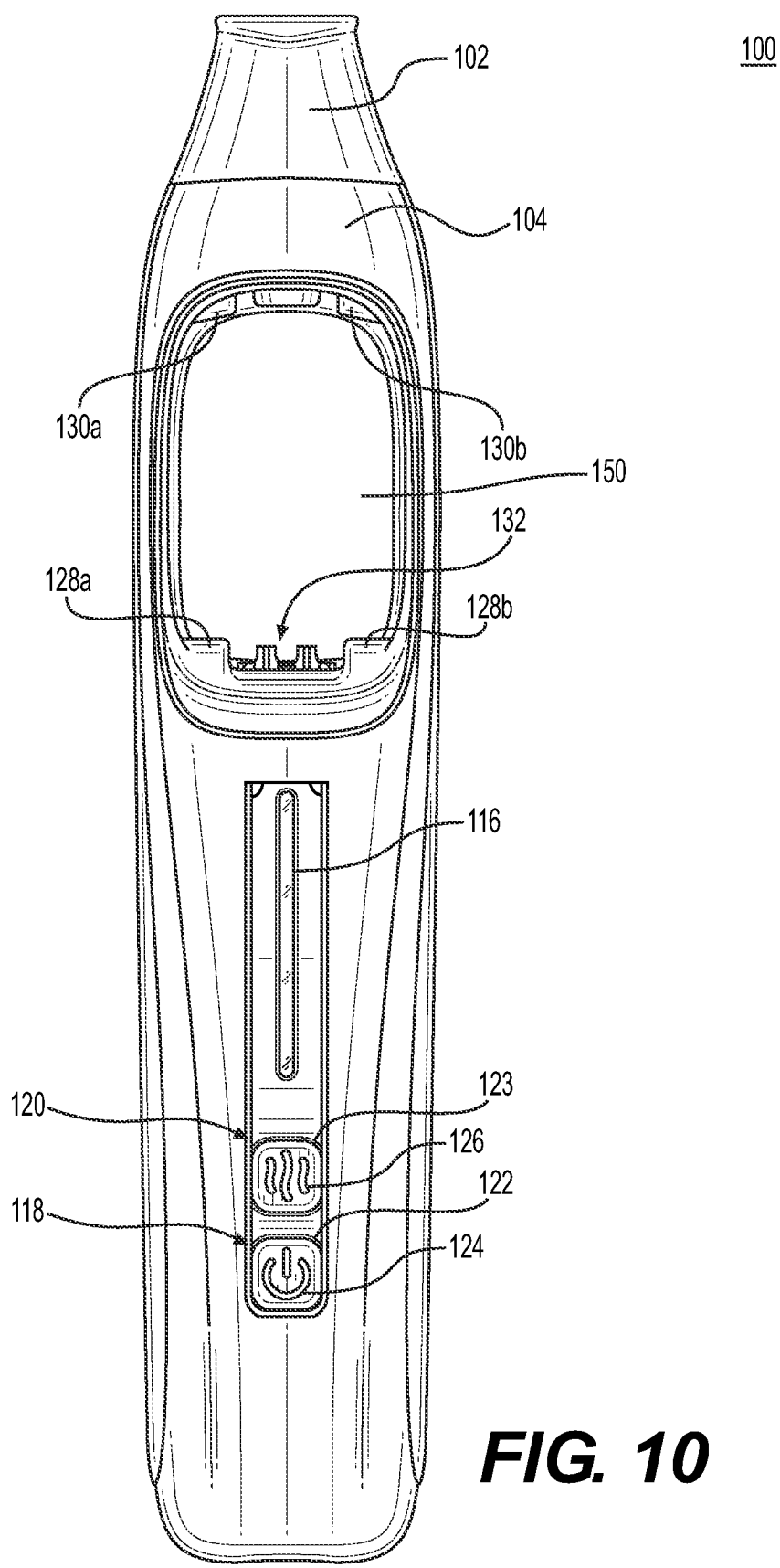
FIG. 10 is a front view of the device body of FIG. 9.

FIG. 10 is a front view of the device body of FIG. 9. Referring to FIG. 10, the device body 100 includes a device electrical connector 132 disposed at an upstream side of the through hole 150. The device electrical connector 132 of the device body 100 is configured to electrically engage with a non-nicotine pod assembly 300 that is seated within the through hole 150. As a result, power can be supplied from the device body 100 to the non-nicotine pod assembly 300 via the device electrical connector 132 during vaping. In addition, data can be sent to and/or received from the device body 100 and the non-nicotine pod assembly 300 via the device electrical connector 132.

Figure 11:
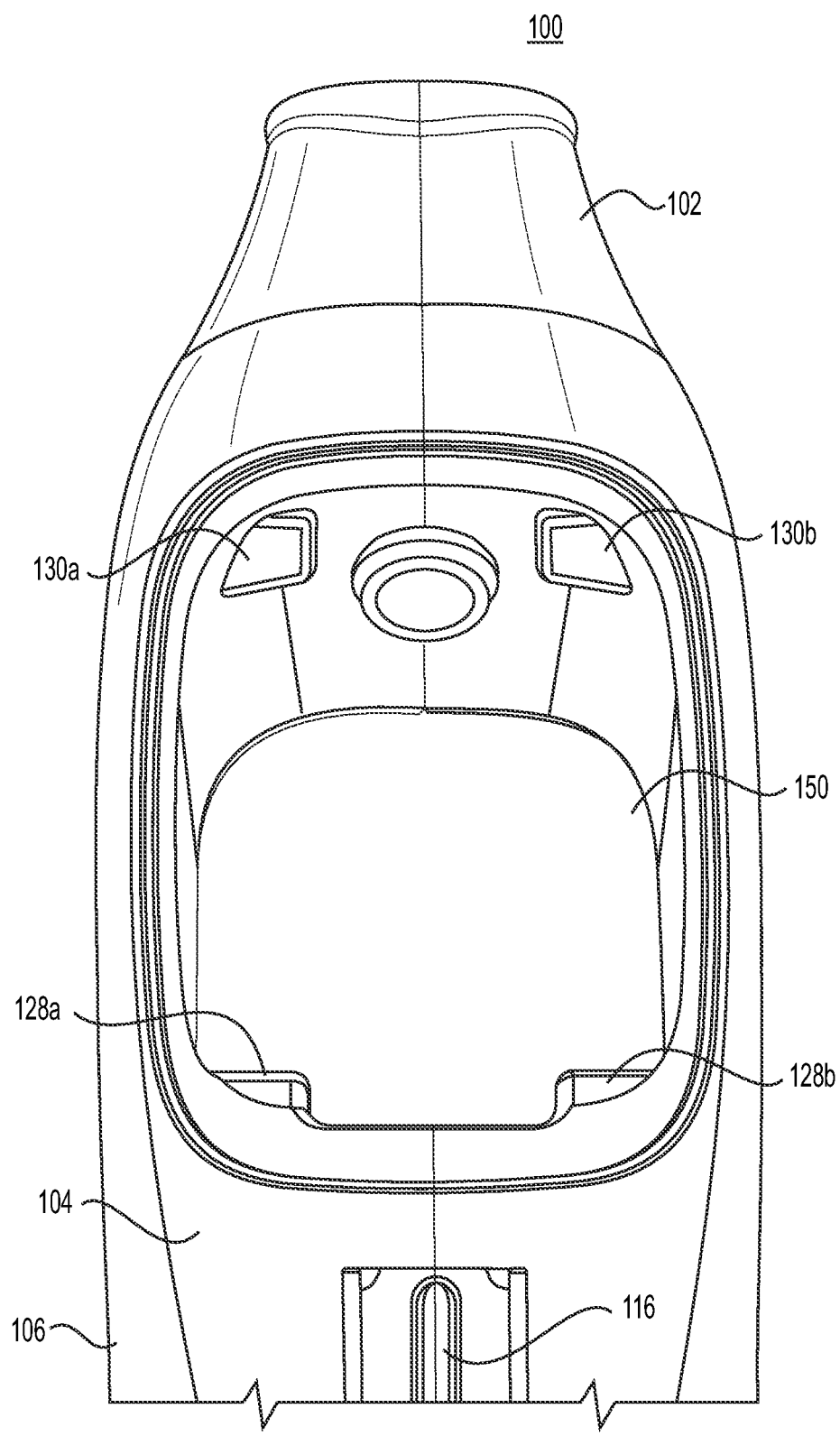
FIG. 11 is an enlarged perspective view of the through hole in FIG. 10.

FIG. 11 is an enlarged perspective view of the through hole in FIG. 10. Referring to FIG. 11, the first upstream protrusion 128a, the second upstream protrusion 128b, the first downstream protrusion 130a, the second downstream protrusion 130b, and the distal end of the mouthpiece 102 protrude into the through hole 150. In an example embodiment, the first upstream protrusion 128a and the second upstream protrusion 128b are stationary structures (e.g., stationary pivots), while the first downstream protrusion 130a and the second downstream protrusion 130b are tractable structures (e.g., retractable members). For instance, the first downstream protrusion 130a and the second downstream protrusion 130b may be configured (e.g., spring-loaded) to default to a protracted state while also configured to transition temporarily to a retracted state (and reversibly back to the protracted state) to facilitate an insertion of a non-nicotine pod assembly 300.

In particular, when inserting a non-nicotine pod assembly 300 into the through hole 150 of the device body 100, recesses at the upstream end face of the non-nicotine pod assembly 300 may be initially engaged with the first upstream protrusion 128a and the second upstream protrusion 128b followed by a pivoting of the non-nicotine pod assembly 300 (about the first upstream protrusion 128a and the second upstream protrusion 128b) until recesses at the downstream end face of the non-nicotine pod assembly 300 are engaged with the first downstream protrusion 130a and the second downstream protrusion 130b. In such an instance, the axis of rotation (during pivoting) of the non-nicotine pod assembly 300 may be orthogonal to the longitudinal axis of the device body 100. In addition, the first downstream protrusion 130a and the second downstream protrusion 130b, which may be biased so as to be tractable, may retract when the non-nicotine pod assembly 300 is being pivoted into the through hole 150 and resiliently protract to engage recesses at the downstream end face of the non-nicotine pod assembly 300. Furthermore, the engagement of the first downstream protrusion 130a and the second downstream protrusion 130b with recesses at the downstream end face of the non-nicotine pod assembly 300 may produce a haptic and/or auditory feedback (e.g., audible click) to notify an adult vaper that the non-nicotine pod assembly 300 is properly seated in the through hole 150 of the device body 100.

Figure 12:
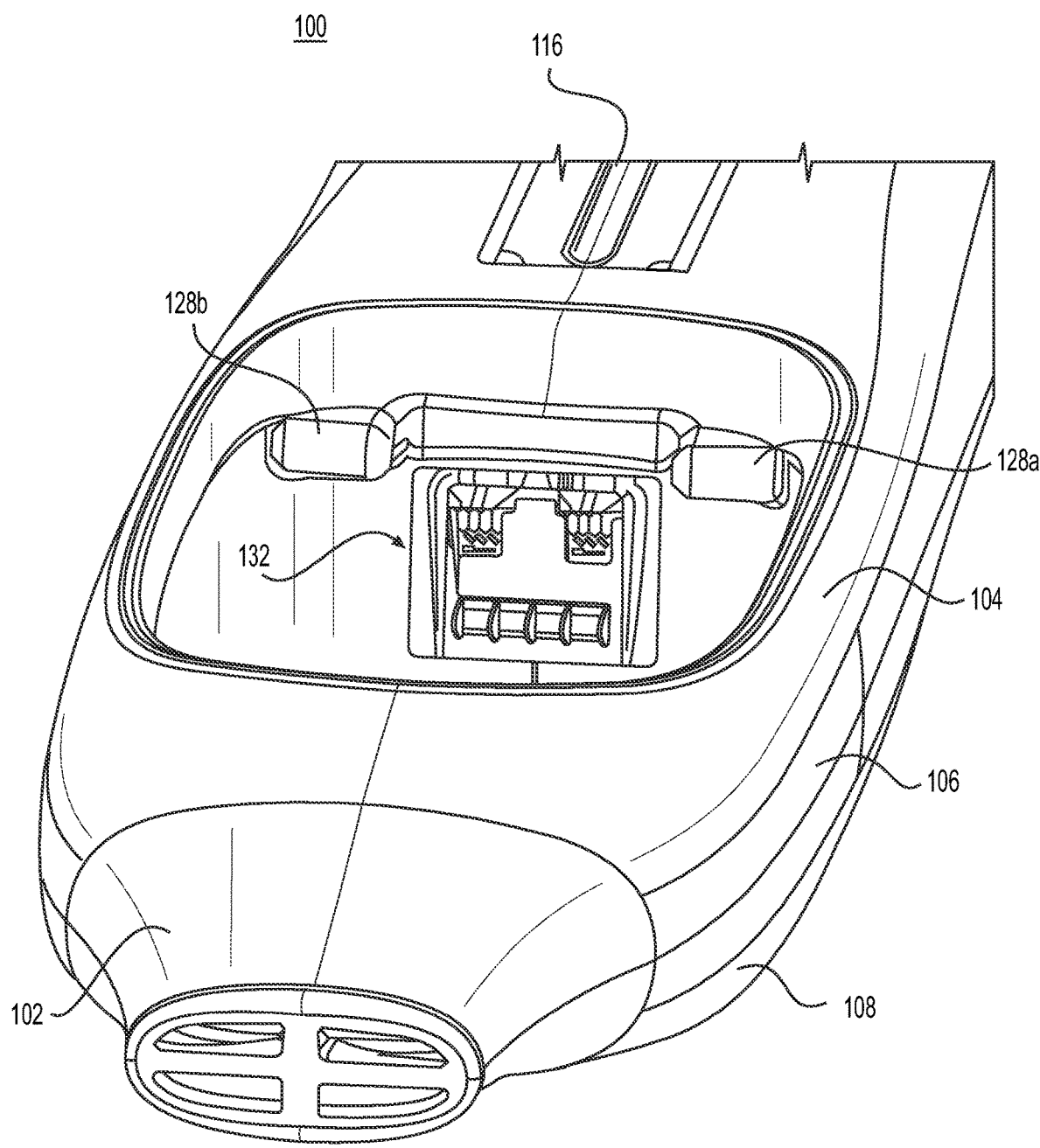
FIG. 12 is an enlarged perspective view of the device electrical contacts in FIG. 10.

FIG. 12 is an enlarged perspective view of the device electrical contacts in FIG. 10. The device electrical contacts of the device body 100 are configured to engage with the pod electrical contacts of the non-nicotine pod assembly 300 when the non-nicotine pod assembly 300 is seated within the through hole 150 of the device body 100. Referring to FIG. 12, the device electrical contacts of the device body 100 include the device electrical connector 132. The device electrical connector 132 includes power contacts and data contacts. The power contacts of the device electrical connector 132 are configured to supply power from the device body 100 to the non-nicotine pod assembly 300. As illustrated, the power contacts of the device electrical connector 132 include a first power contact and a second power contact (which are positioned so as to be closer to the front cover 104 than the rear cover 108). The first power contact (e.g., the power contact adjacent to the first upstream protrusion 128a) may be a single integral structure that is distinct from the second power contact and that, when assembled, includes a projection that extends into the through hole 150. Similarly, the second power contact (e.g., the power contact adjacent to the second upstream protrusion 128b) may be a single integral structure that is distinct from the first power contact and that, when assembled, includes a projection that extends into the through hole 150. The first power contact and the second power contact of the device electrical connector 132 may be tractably-mounted and biased so as to protract into the through hole 150 as a default and to retract (e.g., independently) from the through hole 150 when subjected to a force that overcomes the bias.

The data contacts of the device electrical connector 132 are configured to transmit data between a non-nicotine pod assembly 300 and the device body 100. As illustrated, the data contacts of the device electrical connector 132 include a row of five projections (which are positioned so as to be closer to the rear cover 108 than the front cover 104). The data contacts of the device electrical connector 132 may be distinct structures that, when assembled, extend into the through hole 150. The data contacts of the device electrical connector 132 may also be tractably-mounted and biased (e.g., via a serpentine structure and/or with springs) so as to protract into the through hole 150 as a default and to retract (e.g., independently) from the through hole 150 when subjected to a force that overcomes the bias. For instance, when a non-nicotine pod assembly 300 is inserted into the through hole 150 of the device body 100, the pod electrical contacts of the non-nicotine pod assembly 300 will press against the corresponding device electrical contacts of the device body 100. As a result, the power contacts and the data contacts of the device electrical connector 132 will be retracted (e.g., at least partially retracted) into the device body 100 but will continue to push against the corresponding pod electrical contacts due to their resilient arrangement, thereby helping to ensure a proper electrical connection between the device body 100 and the non-nicotine pod assembly 300. Furthermore, such a connection may also be mechanically secure and have minimal contact resistance so as to allow power and/or signals between the device body 100 and the non-nicotine pod assembly 300 to be transferred and/or communicated reliably and accurately. While various aspects have been discussed in connection with the device electrical contacts of the device body 100, it should be understood that example embodiments are not limited thereto and that other configurations may be utilized.

Figure 13:
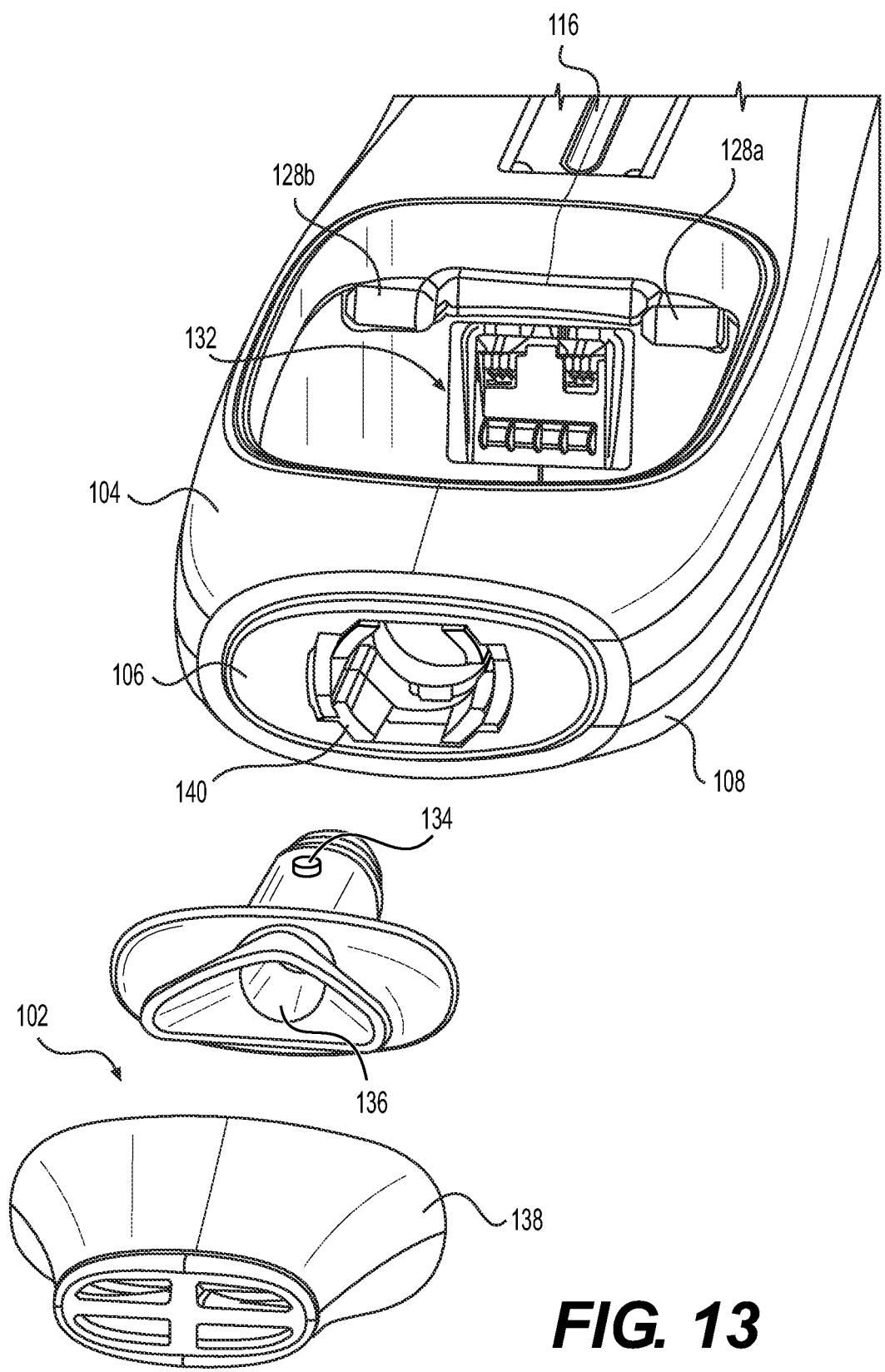
FIG. 13 is a partially exploded view involving the mouthpiece in FIG. 12.

FIG. 13 is a partially exploded view involving the mouthpiece in FIG. 12. Referring to FIG. 13, the mouthpiece 102 is configured to engage with the device housing via a retention structure 140. In an example embodiment, the retention structure 140 is situated so as to be primarily between the frame 106 and the bezel structure 112. As shown, the retention structure 140 is disposed within the device housing such that the proximal end of the retention structure 140 extends through the proximal end of the frame 106. The retention structure 140 may extend slightly beyond the proximal end of the frame 106 or be substantially even therewith. The proximal end of the retention structure 140 is configured to receive a distal end of the mouthpiece 102. The proximal end of the retention structure 140 may be a female end, while the distal end of the mouthpiece may be a male end.

For instance, the mouthpiece 102 may be coupled (e.g., reversibly coupled) to the retention structure 140 with a bayonet connection. In such an instance, the female end of the retention structure 140 may define a pair of opposing L-shaped slots, while the male end of the mouthpiece 102 may have opposing radial members 134 (e.g., radial pins) configured to engage with the L-shaped slots of the retention structure 140. Each of the L-shaped slots of the retention structure 140 may have a longitudinal portion and a circumferential portion. Optionally, the terminus of the circumferential portion may have a serif portion to help reduce or prevent the likelihood that that a radial member 134 of the mouthpiece 102 will inadvertently become disengaged. In a non-limiting embodiment, the longitudinal portions of the L-shaped slots extend in parallel and along a longitudinal axis of the device body 100, while the circumferential portions of the L-shaped slots extend around the longitudinal axis (e.g., central axis) of the device body 100. As a result, to couple the mouthpiece 102 to the device housing, the mouthpiece 102 shown in FIG. 13 is initially rotated 90 degrees to align the radial members 134 with the entrances to the longitudinal portions of the L-shaped slots of the retention structure 140. The mouthpiece 102 is then pushed into the retention structure 140 such that the radial members 134 slide along the longitudinal portions of the L-shaped slots until the junction with each of the circumferential portions is reached. At this point, the mouthpiece 102 is then rotated such that the radial members 134 travel across the circumferential portions until the terminus of each is reached. Where a serif portion is present at each terminus, a haptic and/or auditory feedback (e.g., audible click) may be produced to notify an adult vaper that the mouthpiece 102 has been properly coupled to the device housing.

The mouthpiece 102 defines a vapor passage 136 through which non-nicotine vapor flows during vaping. The vapor passage 136 is in fluidic communication with the through hole 150 (which is where the non-nicotine pod assembly 300 is seated within the device body 100). The proximal end of the vapor passage 136 may include a flared portion. In addition, the mouthpiece 102 may include an end cover 138. The end cover 138 may taper from its distal end to its proximal end. The outlet face of the end cover 138 defines a plurality of vapor outlets. Although four vapor outlets are shown in the end cover 138, it should be understood that example embodiments are not limited thereto.

Figure 14:
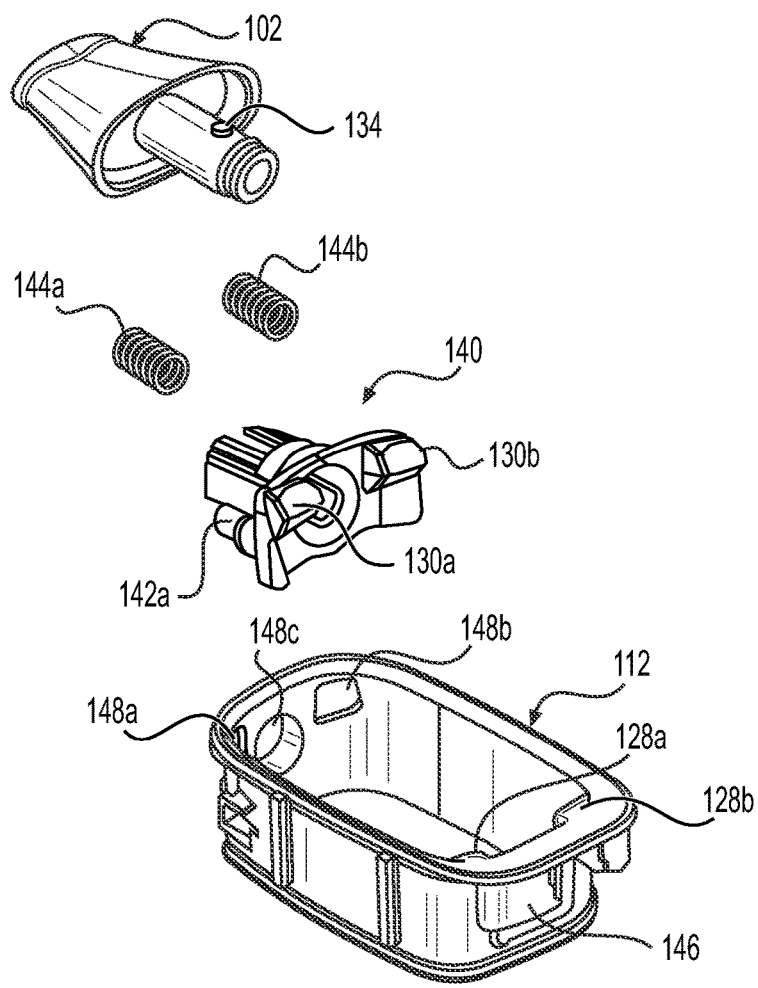
FIG. 14 is a partially exploded view involving the bezel structure in FIG. 9.
Figure 14:
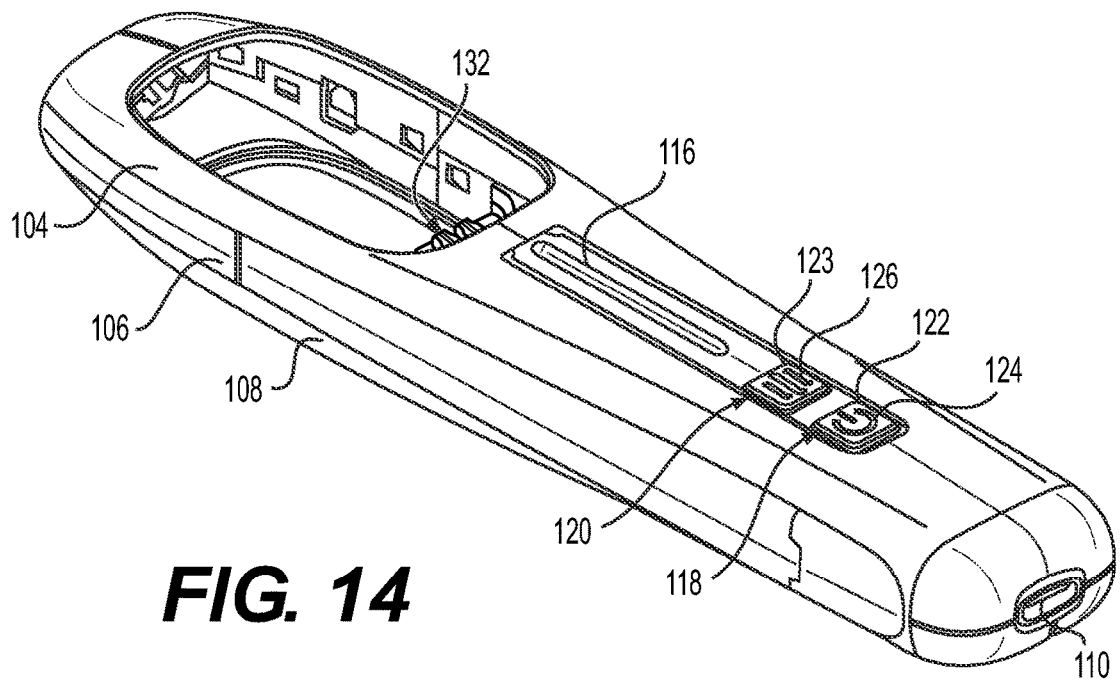
Figure 15:
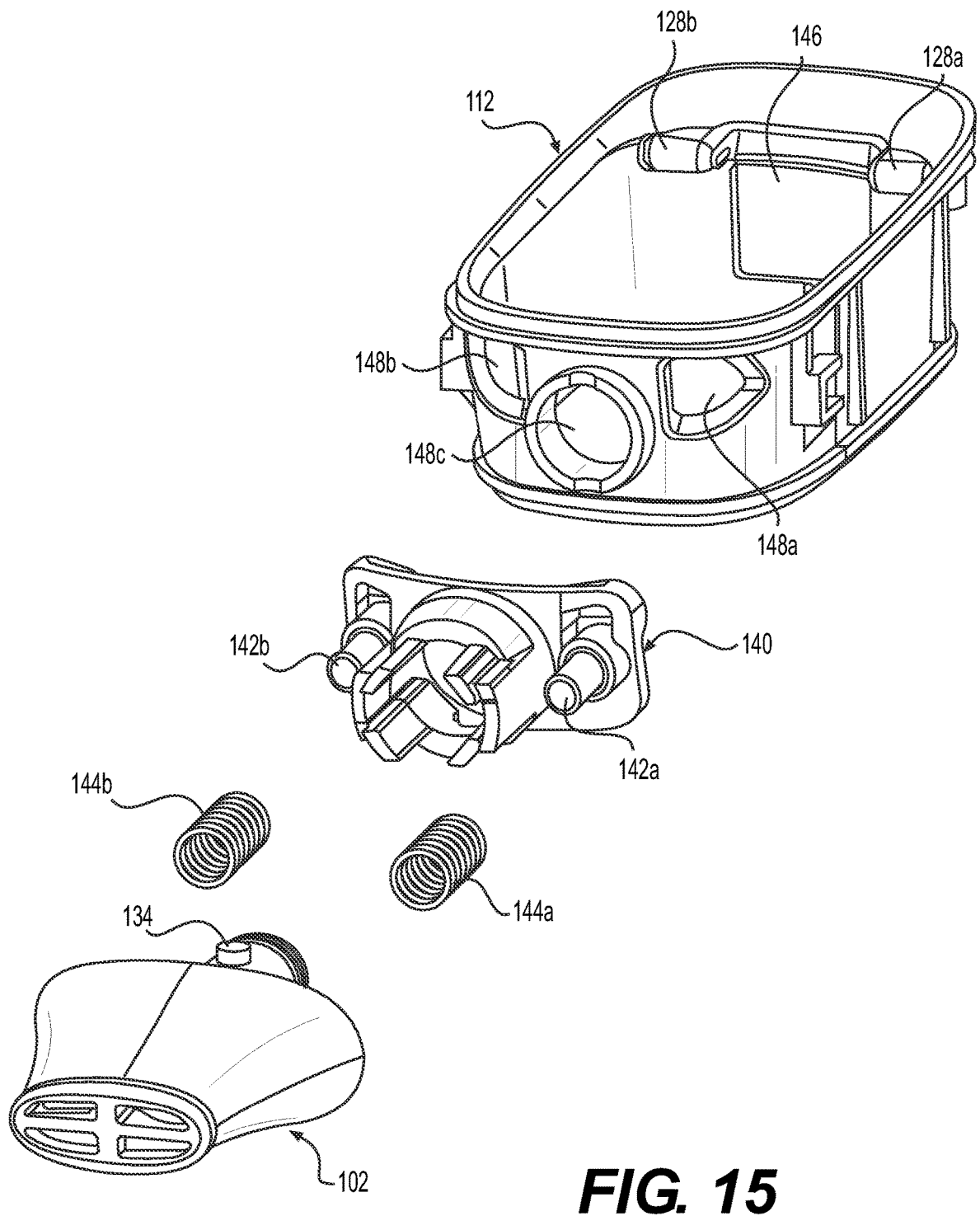
FIG. 15 is an enlarged perspective view of the mouthpiece, springs, retention structure, and bezel structure in FIG. 14.

FIG. 14 is a partially exploded view involving the bezel structure in FIG. 9. FIG. 15 is an enlarged perspective view of the mouthpiece, springs, retention structure, and bezel structure in FIG. 14. Referring to FIGS. 14-15, the bezel structure 112 includes an upstream sidewall and a downstream sidewall. The upstream sidewall of the bezel structure 112 defines a connector opening 146. The connector opening 146 is configured to expose or receive the device electrical connector 132 of the device body 100. The downstream sidewall of the bezel structure 112 defines a first downstream opening 148a, a second downstream opening 148b, and a third downstream opening 148c. The first downstream opening 148a and the second downstream opening 148b of the bezel structure 112 are configured to receive the first downstream protrusion 130a and the second downstream protrusion 130b, respectively, of the retention structure 140. The third downstream opening 148c of the bezel structure 112 is configured to receive the distal end of the mouthpiece 102.

As shown in FIG. 14, the first downstream protrusion 130a and the second downstream protrusion 130b are on the concave side of the retention structure 140. As shown in FIG. 15, a first post 142a and a second post 142b are on the opposing convex side of the retention structure 140. A first spring 144a and a second spring 144b are disposed on the first post 142a and the second post 142b, respectively. The first spring 144a and the second spring 144b are configured to bias the retention structure 140 against the bezel structure 112.

When assembled, the bezel structure 112 may be secured to the frame 106 via a pair of posts on an underside of the upstream rim of the bezel structure 112 and adjacent to the connector opening 146. In addition, the retention structure 140 will abut the bezel structure 112 such that the first downstream protrusion 130a and the second downstream protrusion 130b extend through the first downstream opening 148a and the second downstream opening 148b, respectively. The mouthpiece 102 will be coupled to the retention structure 140 such that the distal end of the mouthpiece 102 extends through the retention structure 140 as well as the third downstream opening 148c of the bezel structure 112. The first spring 144a and the second spring 144b will be between the frame 106 and the retention structure 140.

When a non-nicotine pod assembly 300 is being inserted into the through hole 150 of the device body 100, the downstream end of the non-nicotine pod assembly 300 will push against the first downstream protrusion 130a and the second downstream protrusion 130b of the retention structure 140. As a result, the first downstream protrusion 130a and the second downstream protrusion 130b of the retention structure 140 will resiliently yield and retract from the through hole 150 of the device body 100 (by virtue of compression of the first spring 144a and the second spring 144b), thereby allowing the insertion of the non-nicotine pod assembly 300 to proceed. In an example embodiment, when the first downstream protrusion 130a and the second downstream protrusion 130b are fully retracted from the through hole 150 of the device body 100, the displacement of the retention structure 140 may cause the ends of the first post 142a and the second post 142b to contact the inner end surface of the frame 106. Furthermore, because the mouthpiece 102 is coupled to the retention structure 140, the distal end of the mouthpiece 102 will retract from the through hole 150, thus causing the proximal end of the mouthpiece 102 (e.g., visible portion including the end cover 138) to also shift by a corresponding distance away from the device housing.

Once the non-nicotine pod assembly 300 is adequately inserted such that the first downstream recess and the second downstream recess of the non-nicotine pod assembly 300 reach a position that allows an engagement with the first downstream protrusion 130a and the second downstream protrusion 130b, respectively, the stored energy from the compression of the first spring 144a and the second spring 144b will cause the first downstream protrusion 130a and the second downstream protrusion 130b to resiliently protract and engage with the first downstream recess and the second downstream recess, respectively, of the non-nicotine pod assembly 300. Furthermore, the engagement may produce a haptic and/or auditory feedback (e.g., audible click) to notify an adult vaper that the non-nicotine pod assembly 300 is properly seated within the through hole 150 of the device body 100.

Figure 16:
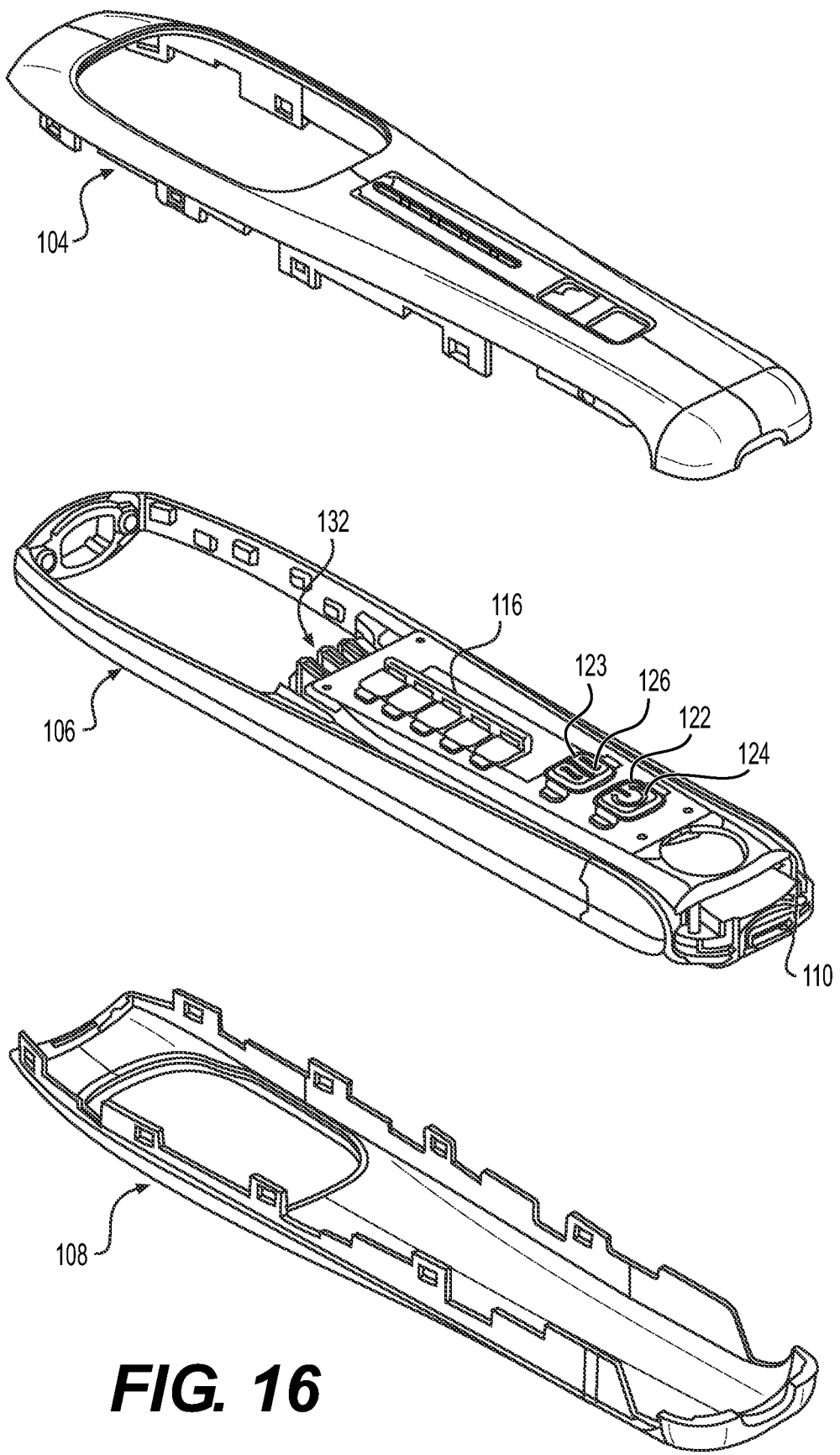
FIG. 16 is a partially exploded view involving the front cover, the frame, and the rear cover in FIG. 14.

FIG. 16 is a partially exploded view involving the front cover, the frame, and the rear cover in FIG. 14. Referring to FIG. 16, various mechanical components, electronic components, and/or circuitry associated with the operation of the non-nicotine e-vaping device 500 may be secured to the frame 106. The front cover 104 and the rear cover 108 may be configured to engage with the frame 106 via a snap-fit arrangement. In an example embodiment, the front cover 104 and the rear cover 108 include clips configured to interlock with corresponding mating members of the frame 106. The clips may be in a form of tabs with orifices configured to receive the corresponding mating members (e.g., protrusions with beveled edges) of the frame 106. In FIG. 16, the front cover 104 has two rows with four clips each (for a total of eight clips for the front cover 104). Similarly, the rear cover 108 has two rows with four clips each (for a total of eight clips for the rear cover 108). The corresponding mating members of the frame 106 may be on the inner sidewalls of the frame 106. As a result, the engaged clips and mating members may be hidden from view when the front cover 104 and the rear cover 108 are snapped together. Alternatively, the front cover 104 and/or the rear cover 108 may be configured to engage with the frame 106 via an interference fit. However, it should be understood that the front cover 104, the frame 106, and the rear cover 108 may be coupled via other suitable arrangements and techniques.

Figure 17:
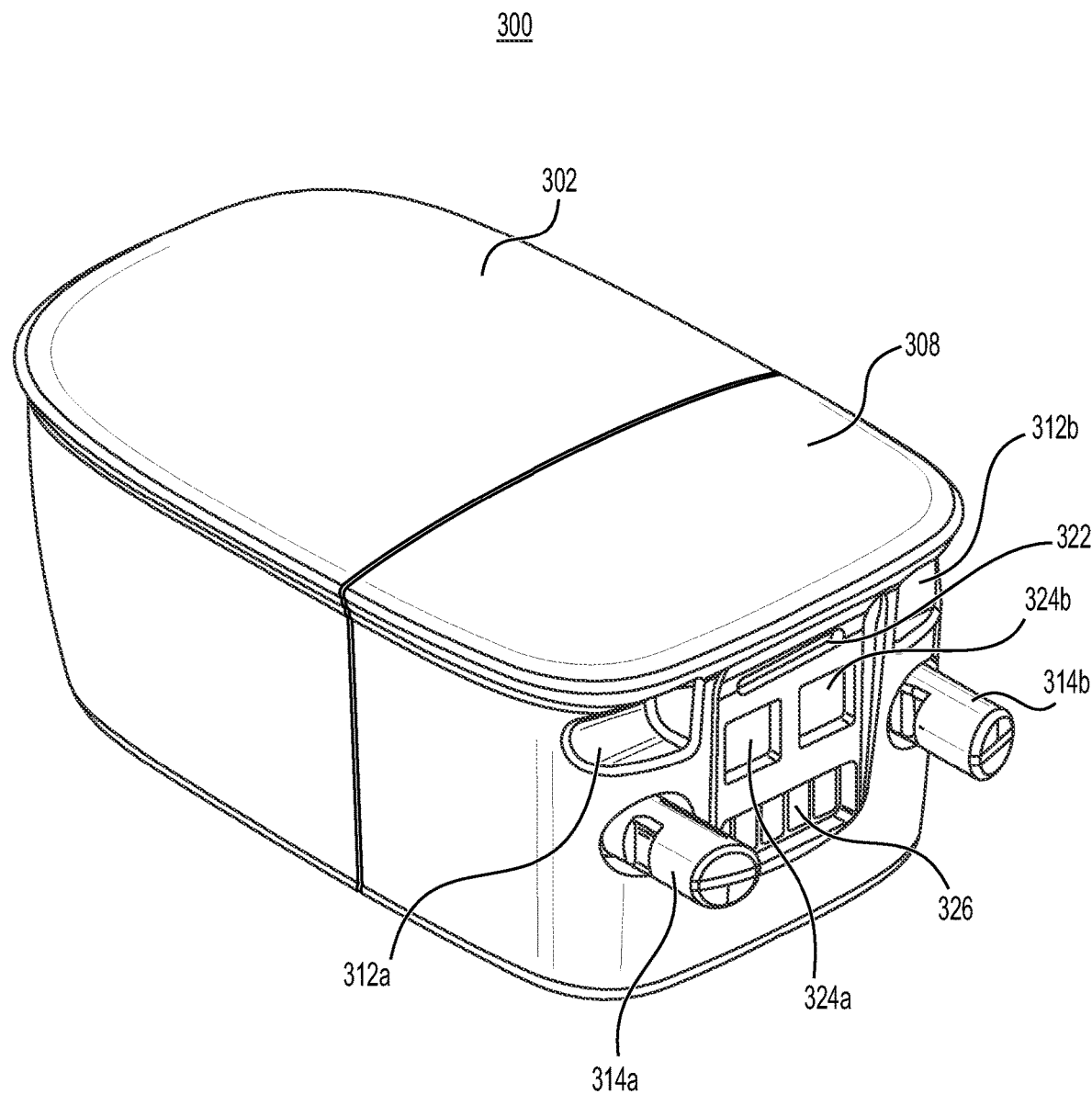
FIG. 17 is a perspective view of the non-nicotine pod assembly of the non-nicotine e-vaping device in FIG. 6.
Figure 18:
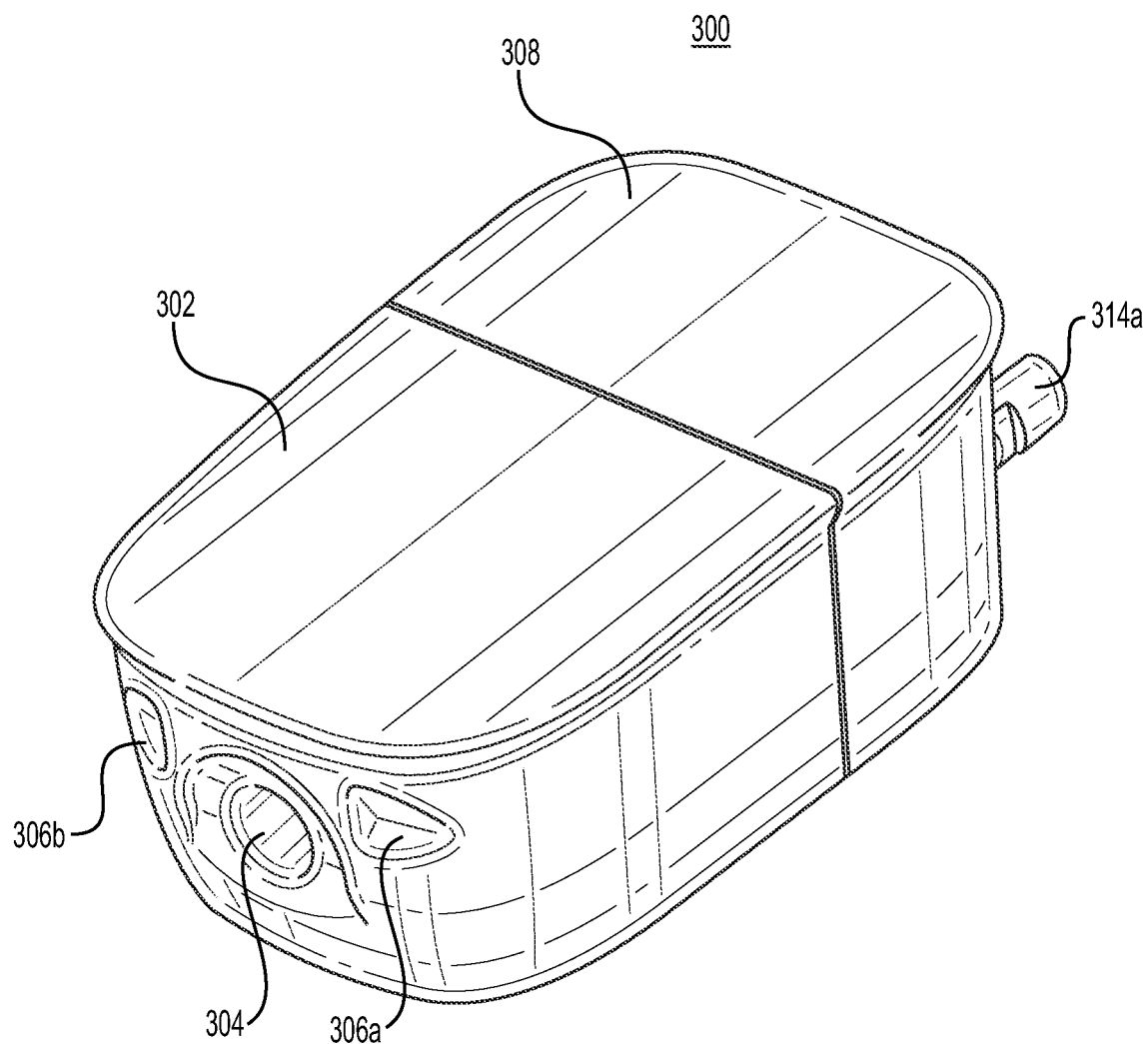
FIG. 18 is another perspective view of the non-nicotine pod assembly of FIG. 17.
Figure 19:
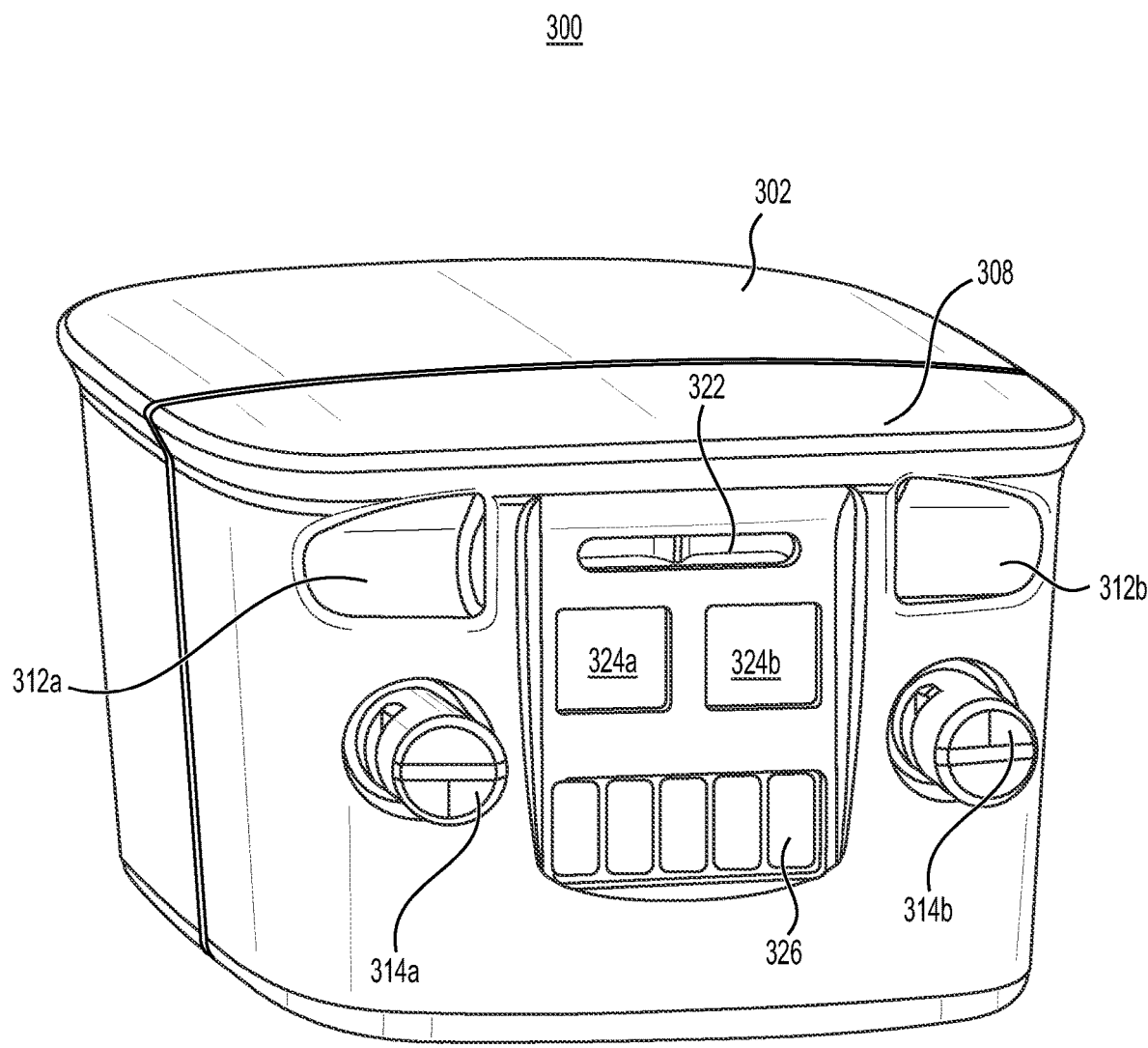
FIG. 19 is another perspective view of the non-nicotine pod assembly of FIG. 18.

FIG. 17 is a perspective view of the non-nicotine pod assembly of the non-nicotine e-vaping device in FIG. 6. FIG. 18 is another perspective view of the non-nicotine pod assembly of FIG. 17. FIG. 19 is another perspective view of the non-nicotine pod assembly of FIG. 18. Referring to FIGS. 17-19, the non-nicotine pod assembly 300 for the non-nicotine e-vaping device 500 includes a pod body configured to hold a non-nicotine pre-vapor formulation. The pod body has an upstream end and a downstream end. The upstream end of the pod body defines a pod inlet 322. The downstream end of the pod body defines a pod outlet 304 that is in fluidic communication with the pod inlet 322 at the upstream end. During vaping, air enters the non-nicotine pod assembly 300 via the pod inlet 322, and non-nicotine vapor exits the non-nicotine pod assembly 300 via the pod outlet 304. The pod inlet 322 is shown in the drawings as being in a form of a slot. However, it should be understood that example embodiments are not limited thereto and that other forms are possible.

The non-nicotine pod assembly 300 includes a connector module 320 (e.g., FIG. 21) that is disposed within the pod body and exposed by openings in the upstream end. The external face of the connector module 320 includes at least one electrical contact. The at least one electrical contact may include a plurality of power contacts. For instance, the plurality of power contacts may include a first power contact 324a and a second power contact 324b. The first power contact 324a of the non-nicotine pod assembly 300 is configured to electrically connect with the first power contact (e.g., the power contact adjacent to the first upstream protrusion 128a in FIG. 12) of the device electrical connector 132 of the device body 100. Similarly, the second power contact 324b of the non-nicotine pod assembly 300 is configured to electrically connect with the second power contact (e.g., the power contact adjacent to the second upstream protrusion 128b in FIG. 12) of the device electrical connector 132 of the device body 100. In addition, the at least one electrical contact of the non-nicotine pod assembly 300 includes a plurality of data contacts 326. The plurality of data contacts 326 of the non-nicotine pod assembly 300 are configured to electrically connect with the data contacts of the device electrical connector 132 (e.g., row of five projections in FIG. 12). While two power contacts and five data contacts are shown in connection with the non-nicotine pod assembly 300, it should be understood that other variations are possible depending on the design of the device body 100.

In an example embodiment, the non-nicotine pod assembly 300 includes a front face, a rear face opposite the front face, a first side face between the front face and the rear face, a second side face opposite the first side face, an upstream end face, and a downstream end face opposite the upstream end face. The corners of the side and end faces (e.g., corner of the first side face and the upstream end face, corner of upstream end face and the second side face, corner of the second side face and the downstream end face, corner of the downstream end face and the first side face) may be rounded. However, in some instances, the corners may be angular. In addition, the peripheral edge of the front face may be in a form of a ledge. The external face of the connector module 320 (that is exposed by the pod body) may be regarded as being part of the upstream end face of the non-nicotine pod assembly 300. The front face of the non-nicotine pod assembly 300 may be wider and longer than the rear face. In such an instance, the first side face and the second side face may be angled inwards towards each other. The upstream end face and the downstream end face may also be angled inwards towards each other. Because of the angled faces, the insertion of the non-nicotine pod assembly 300 will be unidirectional (e.g., from the front side (side associated with the front cover 104) of the device body 100). As a result, the possibility that the non-nicotine pod assembly 300 will be improperly inserted into the device body 100 can be reduced or prevented.

As illustrated, the pod body of the non-nicotine pod assembly 300 includes a first housing section 302 and a second housing section 308. The first housing section 302 has a downstream end defining the pod outlet 304. The rim of the pod outlet 304 may optionally be a sunken or indented region. In such an instance, this region may resemble a cove, wherein the side of the rim adjacent to the rear face of the non-nicotine pod assembly 300 may be open, while the side of the rim adjacent to the front face may be surrounded by a raised portion of the downstream end of the first housing section 302. The raised portion may function as a stopper for the distal end of the mouthpiece 102. As a result, this configuration for the pod outlet 304 may facilitate the receiving and aligning of the distal end of the mouthpiece 102 (e.g., FIG. 11) via the open side of the rim and its subsequent seating against the raised portion of the downstream end of the first housing section 302. In a non-limiting embodiment, the distal end of the mouthpiece 102 may also include (or be formed of) a resilient material to help create a seal around the pod outlet 304 when the non-nicotine pod assembly 300 is properly inserted within the through hole 150 of the device body 100.

The downstream end of the first housing section 302 additionally defines at least one downstream recess. In an example embodiment, the at least one downstream recess is in a form of a first downstream recess 306a and a second downstream recess 306b. The pod outlet 304 may be between the first downstream recess 306a and the second downstream recess 306b. The first downstream recess 306a and the second downstream recess 306b are configured to engage with the first downstream protrusion 130a and the second downstream protrusion 130b, respectively, of the device body 100. As shown in FIG. 11, the first downstream protrusion 130a and the second downstream protrusion 130b of the device body 100 may be disposed on adjacent corners of the downstream sidewall of the through hole 150. The first downstream recess 306a and the second downstream recess 306b may each be in a form of a V-shaped notch. In such an instance, each of the first downstream protrusion 130a and the second downstream protrusion 130b of the device body 100 may be in a form of a wedge-shaped structure configured to engage with a corresponding V-shaped notch of the first downstream recess 306a and the second downstream recess 306b. The first downstream recess 306a may abut the corner of the downstream end face and the first side face, while the second downstream recess 306b may abut the corner of the downstream end face and the second side face. As a result, the edges of the first downstream recess 306a and the second downstream recess 306b adjacent to the first side face and the second side face, respectively, may be open. In such an instance, as shown in FIG. 18, each of the first downstream recess 306a and the second downstream recess 306b may be a 3-sided recess.

The second housing section 308 has an upstream end further defining (in addition to the pod inlet 322) a plurality of openings (e.g., first power contact opening 325a, second power contact opening 325b, data contact opening 327) configured to expose the connector module 320 (FIGS. 20-21) within the non-nicotine pod assembly 300. The upstream end of the second housing section 308 also defines at least one upstream recess. In an example embodiment, the at least one upstream recess is in a form of a first upstream recess 312a and a second upstream recess 312b. The pod inlet 322 may be between the first upstream recess 312a and the second upstream recess 312b. The first upstream recess 312a and the second upstream recess 312b are configured to engage with the first upstream protrusion 128a and the second upstream protrusion 128b, respectively, of the device body 100. As shown in FIG. 12, the first upstream protrusion 128a and the second upstream protrusion 128b of the device body 100 may be disposed on adjacent corners of the upstream sidewall of the through hole 150. A depth of each of the first upstream recess 312a and the second upstream recess 312b may be greater than a depth of each of the first downstream recess 306a and the second downstream recess 306b. A terminus of each of the first upstream recess 312a and the second upstream recess 312b may also be more rounded than a terminus of each of the first downstream recess 306a and the second downstream recess 306b. For instance, the first upstream recess 312a and the second upstream recess 312b may each be in a form of a U-shaped indentation. In such an instance, each of the first upstream protrusion 128a and the second upstream protrusion 128b of the device body 100 may be in a form of a rounded knob configured to engage with a corresponding U-shaped indentation of the first upstream recess 312a and the second upstream recess 312b. The first upstream recess 312a may abut the corner of the upstream end face and the first side face, while the second upstream recess 312b may abut the corner of the upstream end face and the second side face. As a result, the edges of the first upstream recess 312a and the second upstream recess 312b adjacent to the first side face and the second side face, respectively, may be open.

The first housing section 302 may define a reservoir within configured to hold the non-nicotine pre-vapor formulation. The reservoir may be configured to hermetically seal the non-nicotine pre-vapor formulation until an activation of the non-nicotine pod assembly 300 to release the non-nicotine pre-vapor formulation from the reservoir. As a result of the hermetic seal, the non-nicotine pre-vapor formulation may be isolated from the environment as well as the internal elements of the non-nicotine pod assembly 300 that may potentially react with the non-nicotine pre-vapor formulation, thereby reducing or preventing the possibility of adverse effects to the shelf-life and/or sensorial characteristics (e.g., flavor) of the non-nicotine pre-vapor formulation. The second housing section 308 may contain structures configured to activate the non-nicotine pod assembly 300 and to receive and heat the non-nicotine pre-vapor formulation released from the reservoir after the activation.

The non-nicotine pod assembly 300 may be activated manually by an adult vaper prior to the insertion of the non-nicotine pod assembly 300 into the device body 100. Alternatively, the non-nicotine pod assembly 300 may be activated as part of the insertion of the non-nicotine pod assembly 300 into the device body 100. In an example embodiment, the second housing section 308 of the pod body includes a perforator configured to release the non-nicotine pre-vapor formulation from the reservoir in the first housing section 302 during the activation of the non-nicotine pod assembly 300. The perforator may be in a form of a first activation pin 314a and a second activation pin 314b, which will be discussed in more detail herein.

To activate the non-nicotine pod assembly 300 manually, an adult vaper may press the first activation pin 314a and the second activation pin 314b inward (e.g., simultaneously or sequentially) prior to inserting the non-nicotine pod assembly 300 into the through hole 150 of the device body 100. For instance, the first activation pin 314a and the second activation pin 314b may be manually pressed until the ends thereof are substantially even with the upstream end face of the non-nicotine pod assembly 300. In an example embodiment, the inward movement of the first activation pin 314a and the second activation pin 314b causes a seal of the reservoir to be punctured or otherwise compromised so as to release the non-nicotine pre-vapor formulation therefrom.

Alternatively, to activate the non-nicotine pod assembly 300 as part of the insertion of the non-nicotine pod assembly 300 into the device body 100, the non-nicotine pod assembly 300 is initially positioned such that the first upstream recess 312a and the second upstream recess 312b are engaged with the first upstream protrusion 128a and the second upstream protrusion 128b, respectively (e.g., upstream engagement). Because each of the first upstream protrusion 128a and the second upstream protrusion 128b of the device body 100 may be in a form of a rounded knob configured to engage with a corresponding U-shaped indentation of the first upstream recess 312a and the second upstream recess 312b, the non-nicotine pod assembly 300 may be subsequently pivoted with relative ease about the first upstream protrusion 128a and the second upstream protrusion 128b and into the through hole 150 of the device body 100.

With regard to the pivoting of the non-nicotine pod assembly 300, the axis of rotation may be regarded as extending through the first upstream protrusion 128a and the second upstream protrusion 128b and oriented orthogonally to a longitudinal axis of the device body 100. During the initial positioning and subsequent pivoting of the non-nicotine pod assembly 300, the first activation pin 314a and the second activation pin 314b will come into contact with the upstream sidewall of the through hole 150 and transition from a protracted state to a retracted state as the first activation pin 314a and the second activation pin 314b are pushed (e.g., simultaneously) into the second housing section 308 as the non-nicotine pod assembly 300 progresses into the through hole 150. When the downstream end of the non-nicotine pod assembly 300 reaches the vicinity of the downstream sidewall of the through hole 150 and comes into contact with the first downstream protrusion 130a and the second downstream protrusion 130b, the first downstream protrusion 130a and the second downstream protrusion 130b will retract and then resiliently protract (e.g., spring back) when the positioning of the non-nicotine pod assembly 300 allows the first downstream protrusion 130a and the second downstream protrusion 130b of the device body 100 to engage with the first downstream recess 306a and the second downstream recess 306b, respectively, of the non-nicotine pod assembly 300 (e.g., downstream engagement).

As noted supra, according to an example embodiment, the mouthpiece 102 is secured to the retention structure 140 (of which the first downstream protrusion 130a and the second downstream protrusion 130b are a part). In such an instance, the retraction of the first downstream protrusion 130a and the second downstream protrusion 130b from the through hole 150 will cause a simultaneous shift of the mouthpiece 102 by a corresponding distance in the same direction (e.g., downstream direction). Conversely, the mouthpiece 102 will spring back simultaneously with the first downstream protrusion 130a and the second downstream protrusion 130b when the non-nicotine pod assembly 300 has been sufficiently inserted to facilitate downstream engagement. In addition to the resilient engagement by the first downstream protrusion 130a and the second downstream protrusion 130b, the distal end of the mouthpiece 102 is configured to also be biased against the non-nicotine pod assembly 300 (and aligned with the pod outlet 304 so as to form a relatively vapor-tight seal) when the non-nicotine pod assembly 300 is properly seated within the through hole 150 of the device body 100.

Furthermore, the downstream engagement may produce an audible click and/or a haptic feedback to indicate that the non-nicotine pod assembly 300 is properly seated within the through hole 150 of the device body 100. When properly seated, the non-nicotine pod assembly 300 will be connected to the device body 100 mechanically, electrically, and fluidically. Although the non-limiting embodiments herein describe the upstream engagement of the non-nicotine pod assembly 300 as occurring before the downstream engagement, it should be understood that the pertinent mating, activation, and/or electrical arrangements may be reversed such that the downstream engagement occurs before the upstream engagement. The engagement of the non-nicotine pod assembly 300 with the device body 100 as well as other aspects of the non-nicotine e-vaping device 500 may also be as described in U.S. application Ser. No. 16/695,563, titled "Non-nicotine Pod Assemblies And Non-nicotine E-vaping Devices", filed concurrently herewith, the entire contents of which is incorporated herein by reference.

Figure 20:
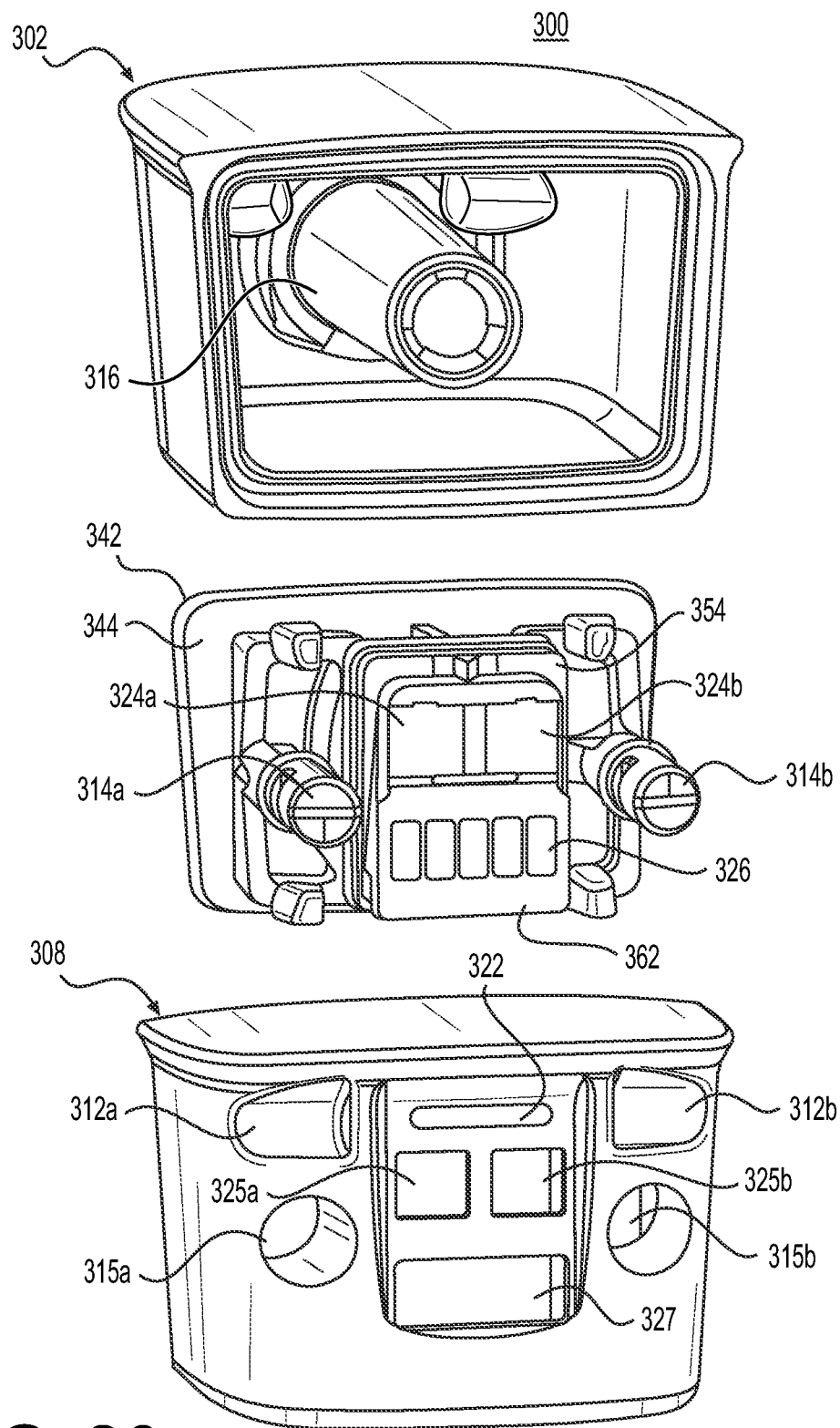
FIG. 20 is a partially exploded view of the non-nicotine pod assembly of FIG. 19.

FIG. 20 is a partially exploded view of the non-nicotine pod assembly of FIG. 19. Referring to FIG. 20, the first housing section 302 includes a vapor channel 316. The vapor channel 316 is configured to receive the non-nicotine vapor generated during vaping and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. An insert 342 and a seal 344 are disposed at an upstream end of the first housing section 302 to define the reservoir of the non-nicotine pod assembly 300. For instance, the insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the non-nicotine pre-vapor formulation in the reservoir. The insert 342 and the seal 344 are also illustrated, for instance, in FIG. 24 and will be discussed in more detail herein.

The upstream end of the second housing section 308 defines a pod inlet 322, a first power contact opening 325a, a second power contact opening 325b, a data contact opening 327, a first upstream recess 312a, a second upstream recess 312b, a first pin opening 315a, and a second pin opening 31b. As noted supra, the pod inlet 322 allows air to enter the non-nicotine pod assembly 300 during vaping, while the first power contact opening 325a, the second power contact opening 325b, and the data contact opening 327 are configured to expose the first power contact 324a, the second power contact 324b, and the data contacts 326, respectively, of the connector module 320. In an example embodiment, the first power contact 324a and the second power contact 324b are mounted on a module housing 354 of the connector module 320. In addition, the data contacts 326 may be disposed on a printed circuit board (PCB) 362. Furthermore, the pod inlet 322 may be situated between the first upstream recess 312a and the second upstream recess 312b, while the contact openings (e.g., first power contact opening 325a, second power contact opening 325b, data contact opening 327) may be situated between the first pin opening 315a and the second pin opening 315b. The first pin opening 315a and the second pin opening 315b are configured to accommodate the first activation pin 314a and the second activation pin 314b, respectively, which extend therethrough.

Figure 21:
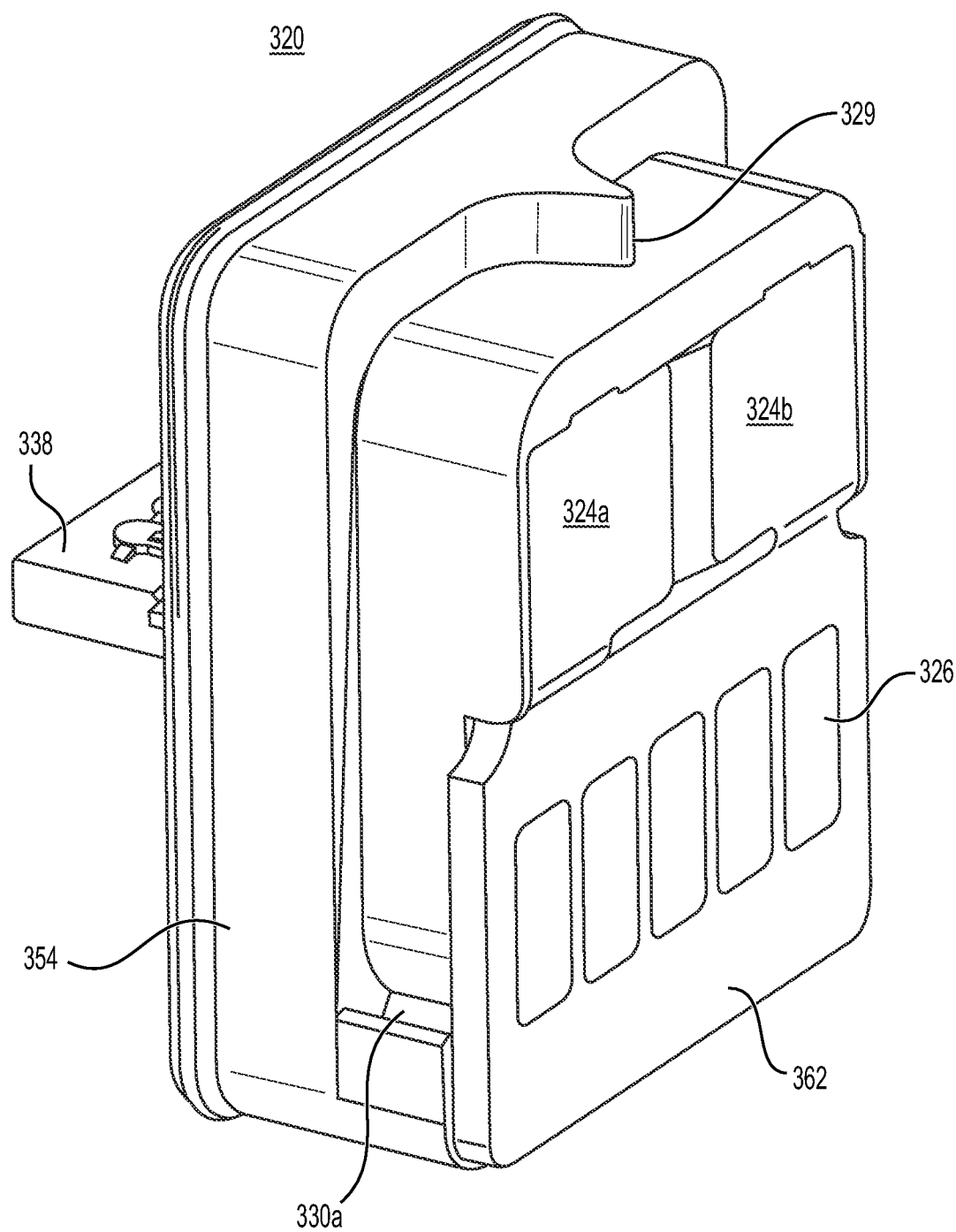
FIG. 21 is a perspective view of the connector module in FIG. 20.
Figure 22:
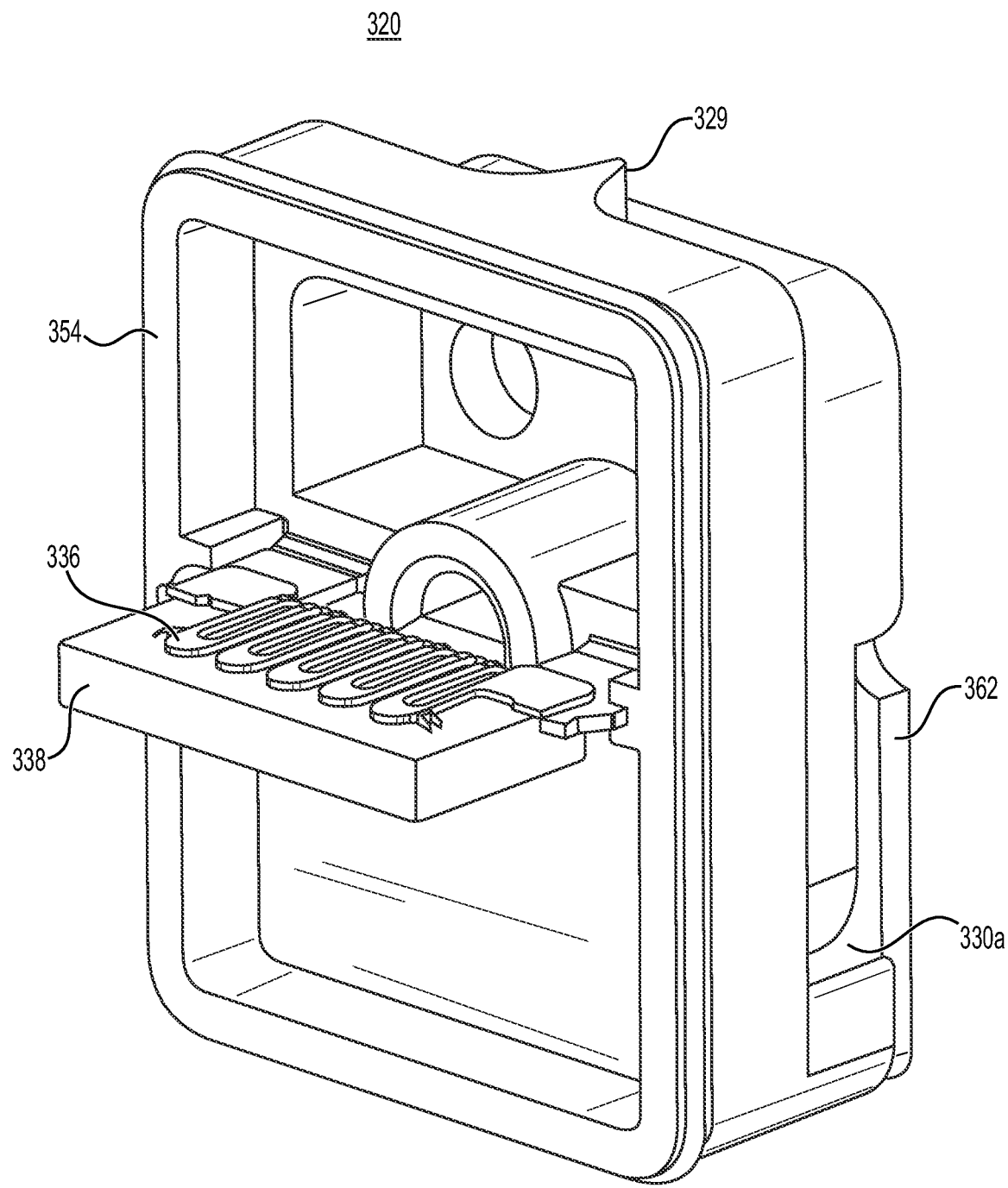
FIG. 22 is another perspective view of the connector module of FIG. 21.

FIG. 21 is a perspective view of the connector module in FIG. 20. FIG. 22 is another perspective view of the connector module of FIG. 21. Referring to FIGS. 21-22, the general framework of the connector module 320 includes a module housing 354. In addition, the connector module 320 has a plurality of faces, including an external face and side faces adjacent to the external face. In an example embodiment, the external face of the connector module 320 is composed of upstream surfaces of the module housing 354, the first power contact 324a, the second power contact 324b, the data contacts 326, and the printed circuit board (PCB) 362. The side faces of the connector module 320 may be integral parts of the module housing 354 and generally orthogonal to the external face.

The non-nicotine pod assembly 300 defines a flow path within from the pod inlet 322 to the pod outlet 304. The flow path through the non-nicotine pod assembly 300 includes, inter alia, a first diverged portion, a second diverged portion, and a converged portion. The pod inlet 322 is upstream from the first diverged portion and the second diverged portion of the flow path. In particular, as shown in FIG. 21, the side face (e.g., inlet side face) of the module housing 354 (and the connector module 320) above the first power contact 324a and the second power contact 324b is recessed so as to define a divider 329 along with initial segments of the first diverged portion and the second diverged portion of the flow path. In an example embodiment where the divider 329 is indented from the external face of the module housing 354 (e.g., FIG. 21), the side face of the module housing 354 above the first power contact 324a and the second power contact 324b may also be regarded as defining an inlet portion of the flow path that is downstream from the pod inlet 322 and upstream from the first diverged portion and the second diverged portion of the flow path.

The pair of longer side faces (e.g., vertical side faces) of the module housing 354 is also recessed so as to define subsequent segments of the first diverged portion and the second diverged portion of the flow path. Herein, the pair of longer side faces of the module housing 354 may be referred to, in the alternative, as lateral faces. The sector of the module housing 354 covered by the printed circuit board (PCB) 362 in FIG. 21 (but shown in FIG. 30) defines further segments of the first diverged portion and the second diverged portion along with the converged portion of the flow path. The further segments of the first diverged portion and the second diverged portion include a first curved segment (e.g., first curved path 330a) and a second curved segment (e.g., second curved path 330b), respectively. As will be discussed in more detail herein, the first diverged portion and the second diverged portion convene to form the converged portion of the flow path.

When the connector module 320 is seated within a receiving cavity in the downstream side of the second housing section 308, the unrecessed side faces of the module housing 354 interface with the sidewalls of the receiving cavity of the second housing section 308, while the recessed side faces of the module housing 354 together with the sidewalls of the receiving cavity define the first diverged portion and the second diverged portion of the flow path. The seating of the connector module 320 within the receiving cavity of the second housing section 308 may be via a close-fit arrangement such that the connector module 320 remains essentially stationary within the non-nicotine pod assembly 300.

As shown in FIG. 22, the connector module 320 includes a wick 338 that is configured to transfer a non-nicotine pre-vapor formulation to a heater 336. The heater 336 is configured to heat the non-nicotine pre-vapor formulation during vaping to generate a non-nicotine vapor. The heater 336 is electrically connected to at least one electrical contact of the connector module 320. For instance, one end (e.g., first end) of the heater 336 may be connected to the first power contact 324a, while the other end (e.g., second end) of the heater 336 may be connected to the second power contact 324b. In an example embodiment, the heater 336 includes a folded heating element. In such an instance, the wick 338 may have a planar form configured to be held by the folded heating element. When the non-nicotine pod assembly 300 is assembled, the wick 338 is configured to be in fluidic communication with an absorbent material 346 (e.g., FIG. 25) such that the non-nicotine pre-vapor formulation that will be in the absorbent material 346 (when the non-nicotine pod assembly 300 is activated) will be transferred to the wick 338 via capillary action.

In an example embodiment, an incoming air flow entering the non-nicotine pod assembly 300 through the pod inlet 322 is directed by the divider 329 into the first diverged portion and the second diverged portion of the flow path. The divider 329 may be wedge-shaped and configured to split the incoming air flow into opposite directions (e.g., at least initially). The split air flow may include a first air flow (that travels through the first diverged portion of the flow path) and a second air flow (that travels through the second diverged portion of the flow path). Following the split by the divider 329, the first air flow travels along the inlet side face and continues around the corner to and along the first lateral face to the first curved path 330a. Similarly, the second air flow travels along the inlet side face and continues around the corner to and along the second lateral face to the second curved path 330b (e.g., FIG. 30). The converged portion of the flow path is downstream from the first diverged portion and the second diverged portion. The heater 336 and the wick 338 are downstream from the converged portion of the flow path. Thus, the first air flow joins with the second air flow in the converged portion (e.g., converged path 330c in FIG. 30) of the flow path to form a combined flow before passing through a module outlet 368 (e.g., labeled in FIG. 28) in the module housing 354 to the heater 336 and the wick 338.

Figure 23:
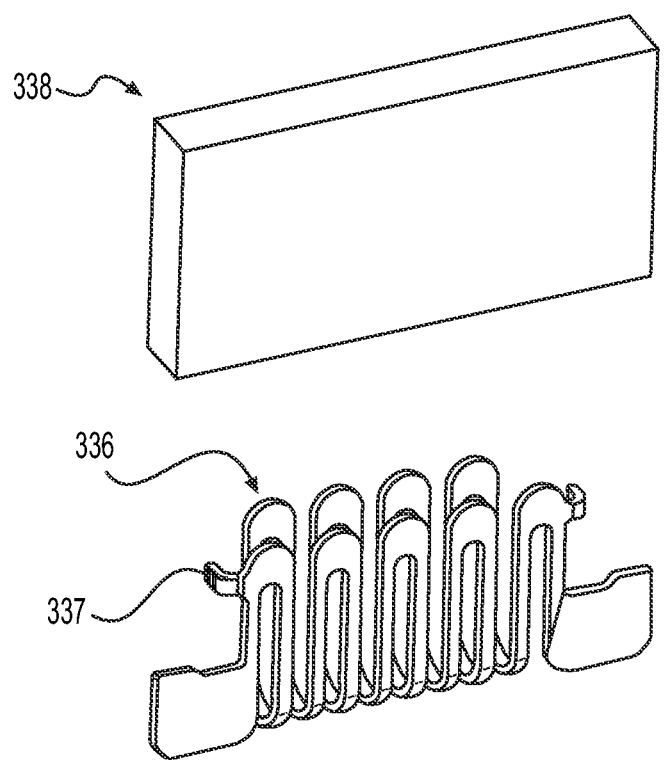
FIG. 23 is an exploded view involving the wick and heater in FIG. 22.

FIG. 23 is an exploded view involving the wick and heater in FIG. 22. Referring to FIG. 23, the wick 338 may be a fibrous pad or other structure with pores/interstices designed for capillary action. In addition, the wick 338 may have a rectangular shape, although example embodiments are not limited thereto. For instance, the wick 338 may have an alternative shape of an irregular hexagon, wherein two of the sides are angled inward and toward the heater 336. The wick 338 may be fabricated into the desired shape or cut from a larger sheet of material into such a shape. Where the lower section of the wick 338 is tapered towards the winding section of the heater 336 (e.g., hexagon shape), the likelihood of the non-nicotine pre-vapor formulation being in a part of the wick 338 that continuously evades vaporization (due to its distance from the heater 336) can be reduced or avoided. Furthermore, as noted supra, the heater 336 may include a folded heating element configured to grip the wick 338. The folded heating element may also include at least one prong 337 configured to protrude into the wick 338.

In an example embodiment, the heater 336 is configured to undergo Joule heating (which is also known as ohmic/resistive heating) upon the application of an electric current thereto. Stated in more detail, the heater 336 may be formed of one or more conductors (resistive materials) and configured to produce heat when an electric current passes therethrough. The electric current may be supplied from a power source (e.g., battery) within the device body 100 and conveyed to the heater 336 via the first power contact 324a or the second power contact 324b.

Suitable conductors (resistive materials) for the heater 336 include an iron-based alloy (e.g., stainless steel) and/or a nickel-based alloy (e.g., nichrome). The heater 336 may be fabricated from a conductive sheet (e.g., metal, alloy) that is stamped to cut a winding pattern therefrom. The winding pattern may have curved segments alternately arranged with horizontal segments so as to allow the horizontal segments to zigzag back and forth while extending in parallel. In addition, a width of each of the horizontal segments of the winding pattern may be substantially equal to a spacing between adjacent horizontal segments of the winding pattern, although example embodiments are not limited thereto. To obtain the form of the heater 336 shown in the drawings, the winding pattern may be folded so as to grip the wick 338. Additionally, when the prongs 337 are part of the heater 336, the projections corresponding to the prongs 337 are bent (e.g., inward and/or orthogonally) before the winding pattern is folded. As a result of the prongs 337, the possibility that the wick 338 will slip out of the heater 336 will be reduced or prevented. The heater and associated structures are discussed in more detail in U.S. application Ser. No. 15/729,909, titled "Folded Heater For Electronic Vaping Device", filed Oct. 11, 2017, the entire contents of which is incorporated herein by reference.

Figure 24:
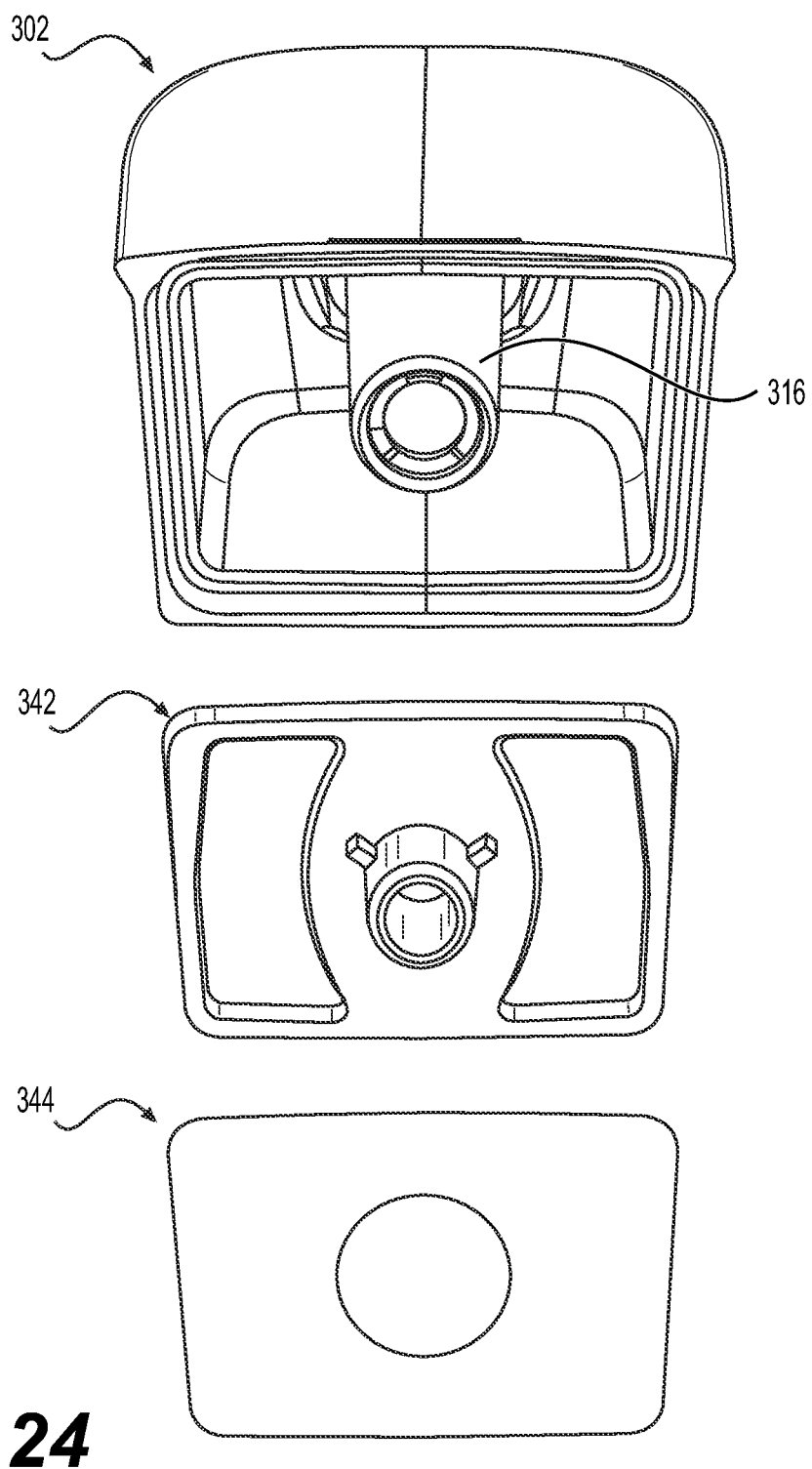
FIG. 24 is an exploded view involving the first housing section of the non-nicotine pod assembly of FIG. 17.

FIG. 24 is an exploded view involving the first housing section of the non-nicotine pod assembly of FIG. 17. Referring to FIG. 24, the first housing section 302 includes a vapor channel 316. The vapor channel 316 is configured to receive non-nicotine vapor generated by the heater 336 and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. An insert 342 and a seal 344 are disposed at an upstream end of the first housing section 302 to define the reservoir of the non-nicotine pod assembly 300. For instance, the insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the non-nicotine pre-vapor formulation in the reservoir. Herein, the first housing section 302, the insert 342, and the seal 344 may be referred to collectively as the first section. As will be discussed in more detail herein, the first section is configured to hermetically seal the non-nicotine pre-vapor formulation until an activation of the non-nicotine pod assembly 300.

In an example embodiment, the insert 342 includes a holder portion that projects from the upstream side (as shown in FIG. 24) and a connector portion that projects from the downstream side (hidden from view in FIG. 24). The holder portion of the insert 342 is configured to hold the absorbent material 346 (e.g., FIG. 25), while the connector portion of the insert 342 is configured to engage with the vapor channel 316 of the first housing section 302. The connector portion of the insert 342 may be configured to be seated within the vapor channel 316 and, thus, engage the interior of the vapor channel 316. Alternatively, the connector portion of the insert 342 may be configured to receive the vapor channel 316 and, thus, engage with the exterior of the vapor channel 316. The insert 342 also defines reservoir outlets through which the non-nicotine pre-vapor formulation flows when the seal 344 is punctured during the activation of the non-nicotine pod assembly 300. The holder portion and the connector portion of the insert 342 may be between the reservoir outlets (e.g., first and second reservoir outlets), although example embodiments are not limited thereto. Furthermore, the insert 342 defines a vapor conduit extending through the holder portion and the connector portion. As a result, when the insert 342 is seated within the first housing section 302, the vapor conduit of the insert 342 will be aligned with and in fluidic communication with the vapor channel 316 so as to form a continuous path through the reservoir to the pod outlet 304 for the non-nicotine vapor generated by the heater 336 during vaping.

The seal 344 is attached to the upstream side of the insert 342 so as to cover the reservoir outlets in the insert 342. In an example embodiment, the seal 344 defines an opening (e.g., central opening) configured to provide the pertinent clearance to accommodate the holder portion (that projects from the upstream side of the insert 342) when the seal 344 is attached to the insert 342. When the seal 344 is punctured by the first activation pin 314a and the second activation pin 314b of the non-nicotine pod assembly 300, the two punctured sections of the seal 344 will be pushed into the reservoir as flaps, thus creating two punctured openings (e.g., one on each side of the central opening) in the seal 344. The size and shape of the punctured openings in the seal 344 may correspond to the size and shape of the reservoir outlets in the insert 342. In contrast, when in an unpunctured state as shown in FIG. 24, the seal 344 will have a planar form and only one opening (e.g., central opening). The seal 344 is designed to be strong enough to remain intact during the normal movement and/or handling of the non-nicotine pod assembly 300 so as to avoid being prematurely/inadvertently breached. For instance, the seal 344 may be a coated foil (e.g., aluminum-backed polyethylene terephthalate (PET)).

Figure 25:
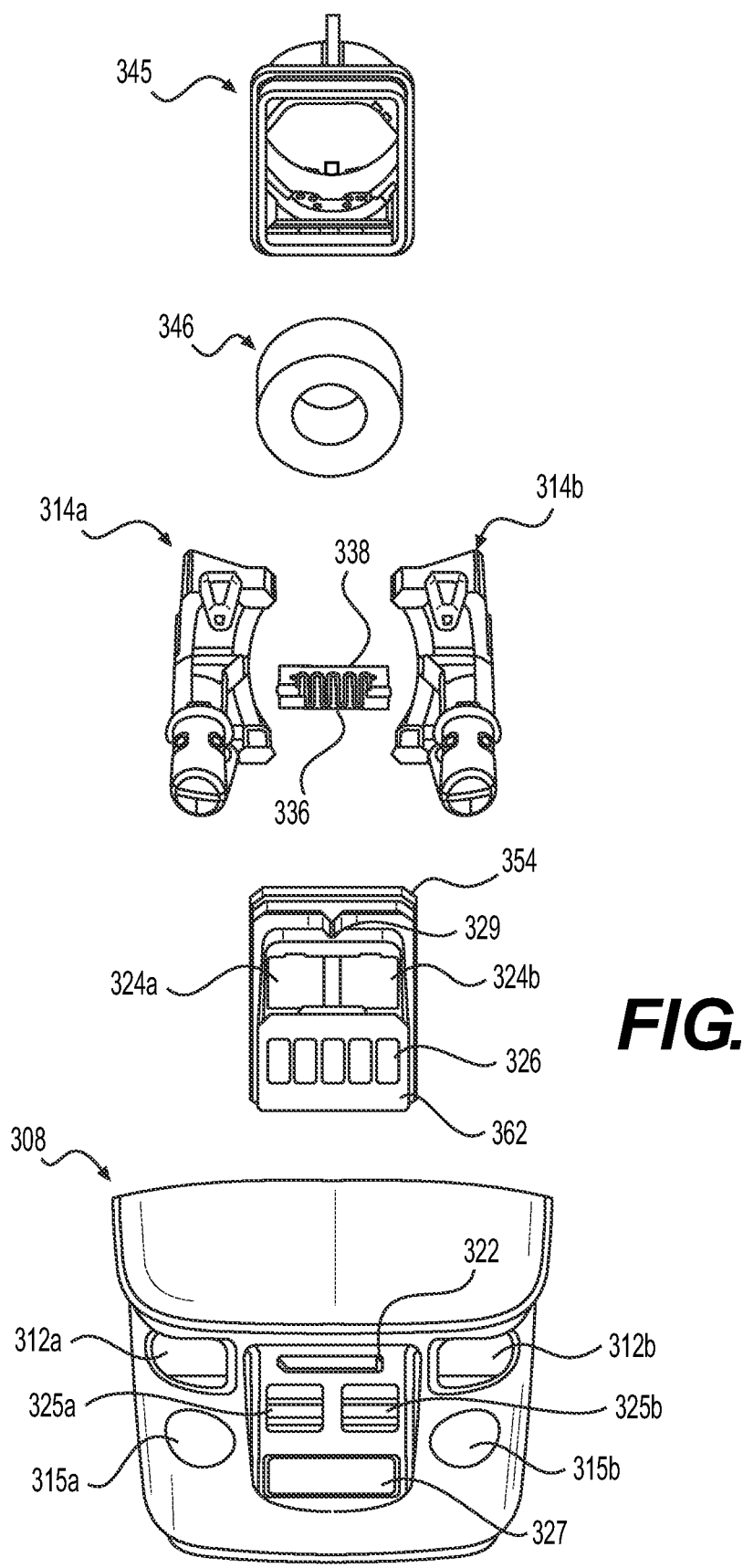
FIG. 25 is a partially exploded view involving the second housing section of the non-nicotine pod assembly of FIG. 17.

FIG. 25 is a partially exploded view involving the second housing section of the non-nicotine pod assembly of FIG. 17. Referring to FIG. 25, the second housing section 308 is structured to contain various components configured to release, receive, and heat the non-nicotine pre-vapor formulation. For instance, the first activation pin 314a and the second activation pin 314b are configured to puncture the reservoir in the first housing section 302 to release the non-nicotine pre-vapor formulation. Each of the first activation pin 314a and the second activation pin 314b has a distal end that extends through a corresponding one of the first pin opening 315a and the second pin opening 315b in the second housing section 308. In an example embodiment, the distal ends of the first activation pin 314a and the second activation pin 314b are visible after assembly (e.g., FIG. 17), while the remainder of the first activation pin 314a and the second activation pin 314b are hidden from view within the non-nicotine pod assembly 300. In addition, each of the first activation pin 314a and the second activation pin 314b has a proximal end that is positioned so as to be adjacent to and upstream from the seal 344 prior to activation of the non-nicotine pod assembly 300. When the first activation pin 314a and the second activation pin 314b are pushed into the second housing section 308 to activate the non-nicotine pod assembly 300, the proximal end of each of the first activation pin 314a and the second activation pin 314b will advance through the insert 342 and, as a result, puncture the seal 344, which will release the non-nicotine pre-vapor formulation from the reservoir. The movement of the first activation pin 314a may be independent of the movement of the second activation pin 314b (and vice versa). The first activation pin 314a and the second activation pin 314b will be discussed in more detail herein.

The absorbent material 346 may be seated within a holder (e.g., top hat holder 345). The absorbent material 346 is also downstream from and in fluidic communication with the wick 338. Furthermore, as noted supra, the absorbent material 346 is configured to engage with the holder portion of the insert 342 (which, as shown in FIG. 24, projects from the upstream side of the insert 342). The absorbent material 346 may have an annular form, although example embodiments are not limited thereto. As depicted in FIG. 25, the absorbent material 346 may resemble a hollow cylinder. In such an instance, the outer diameter of the absorbent material 346 may be substantially equal to (or slightly larger than) the length of the wick 338. The inner diameter of the absorbent material 346 may be smaller than the average outer diameter of the holder portion of the insert 342 so as to result in an interference fit. To facilitate the engagement with the absorbent material 346, the tip of the holder portion of the insert 342 may be tapered. The absorbent material 346 is configured to receive and hold a quantity of the non-nicotine pre-vapor formulation released from the reservoir when the non-nicotine pod assembly 300 is activated.

The wick 338 is positioned within the non-nicotine pod assembly 300 so as to be in fluidic communication with the absorbent material 346 such that the non-nicotine pre-vapor formulation can be drawn from the absorbent material 346 to the heater 336 via capillary action. The wick 338 may physically contact an upstream side of the absorbent material 346 (e.g., bottom of the absorbent material 346 based on the view shown in FIG. 25). In addition, the wick 338 may be aligned with a diameter of the absorbent material 346, although example embodiments are not limited thereto.

As illustrated in FIG. 25 (as well as previous FIG. 23), the heater 336 may have a folded configuration so as to grip and establish thermal contact with the opposing surfaces of the wick 338. The heater 336 is configured to heat the wick 338 during vaping to generate a non-nicotine vapor. To facilitate such heating, the first end of the heater 336 may be electrically connected to the first power contact 324a, while the second end of the heater 336 may be electrically connected to the second power contact 324b. As a result, an electric current may be supplied from a power source (e.g., battery) within the device body 100 and conveyed to the heater 336 via the first power contact 324a or the second power contact 324b. The relevant details of other aspects of the connector module 320 that have already been discussed supra (e.g., in connection with FIGS. 21-22) will not be repeated in this section in the interest of brevity. In an example embodiment, although hidden from view in FIG. 25, the second housing section 308 includes a receiving cavity for the connector module 320. Collectively, the second housing section 308 and the above-discussed components therein may be referred to as the second section. During vaping, the non-nicotine vapor generated by the heater 336 is drawn through the vapor conduit of the insert 342, through the vapor channel 316 of the first housing section 302, out the pod outlet 304 of the non-nicotine pod assembly 300, and through the vapor passage 136 of the mouthpiece 102 to the vapor outlet(s).

Figure 26:
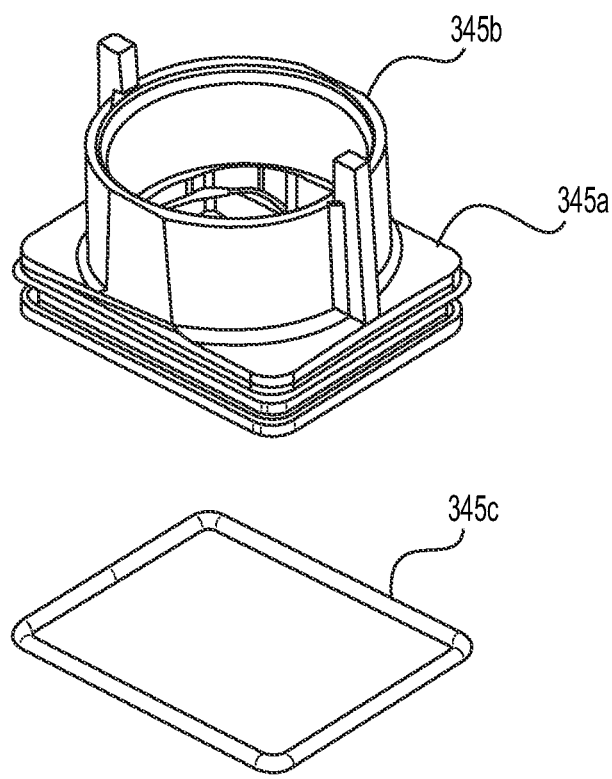
FIG. 26 is an exploded view of the top hat holder in FIG. 25.

FIG. 26 is an exploded view of the top hat holder in FIG. 25. Referring to FIG. 26, the top hat holder 345 includes a base portion 345a and a cylindrical portion 34b. In an example embodiment, the base portion 345a and the cylindrical portion 345b are integrally formed. The cylindrical portion 345b defines a well configured to receive the absorbent material 346. Optionally, the inner, lower surface of the well may include a ledge (or other projection) to support the absorbent material 346 such that the absorbent material 346 does not simply slide through or sag from the top hat holder 345 (e.g., when the absorbent material 346 is saturated with the non-nicotine pre-vapor formulation released from the reservoir). In addition, the base portion 345a defines a groove configured to receive a gasket 345c. Furthermore, a pair of integrally formed posts may extend from the base portion 345a and along the exterior of the cylindrical portion 345b so as to protrude beyond the rim of the cylindrical portion 34b. When the top hat holder 345 is assembled within the non-nicotine pod assembly 300, these pair of integrally formed posts may abut an underside of the insert 342 with a portion of the seal 344 therebetween.

Figure 27:
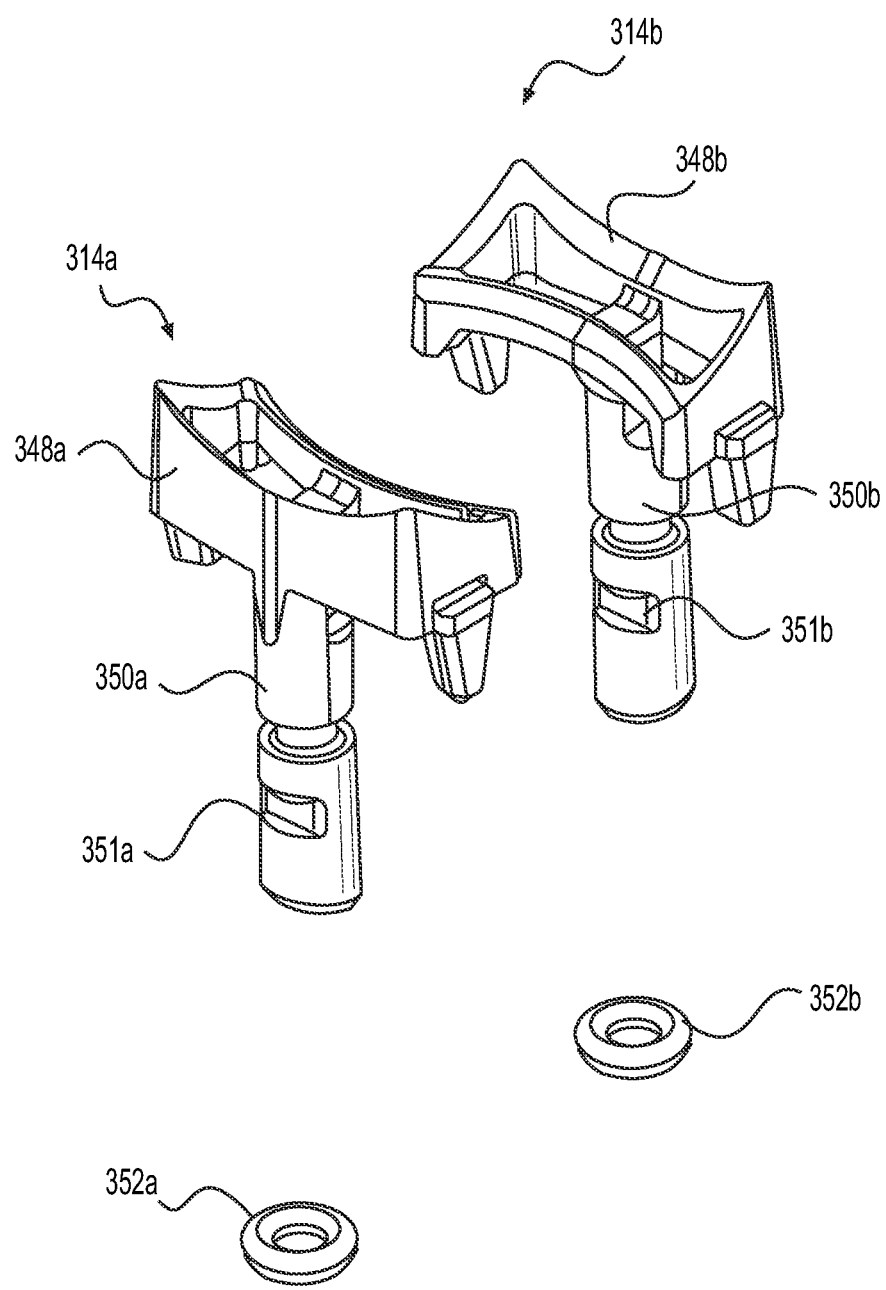
FIG. 27 is an exploded view of the activation pin in FIG. 25.

FIG. 27 is an exploded view of the activation pin in FIG. 25. Referring to FIG. 27, the activation pin may be in the form of a first activation pin 314a and a second activation pin 314b. While two activation pins are shown and discussed in connection with the non-limiting embodiments herein, it should be understood that, alternatively, the non-nicotine pod assembly 300 may include only one activation pin. In FIG. 27, the first activation pin 314a may include a first blade 348a, a first actuator 350a, and a first O-ring 352a. Similarly, the second activation pin 314b may include a second blade 348b, a second actuator 350b, and a second O-ring 352b.

In an example embodiment, the first blade 348a and the second blade 348b are integrally formed with the first actuator 350a and the second actuator 350b, respectively. Alternatively, the first blade 348a and the second blade 348b may be configured to be mounted or attached to upper portions (e.g., proximal portions) of the first actuator 350a and the second actuator 350b, respectively. The mounting or attachment may be achieved via a snap-fit connection, an interference fit (e.g., friction fit) connection, an adhesive, or other suitable coupling technique. The top of each of the first blade 348a and the second blade 348b may have one or more curved or concave edges that taper upward to a pointed tip. For instance, each of the first blade 348a and the second blade 348b may have two pointed tips with a concave edge therebetween and a curved edge adjacent to each pointed tip. The radii of curvature of the concave edge and the curved edges may be the same, while their arc lengths may differ. The first blade 348a and the second blade 348b may be formed of a sheet metal (e.g., stainless steel) that is cut or otherwise shaped to have the desired profile and bent to its final form. In another instance, the first blade 348a and the second blade 348b may be formed of plastic (e.g., when integrally formed with the first actuator 350a and the second actuator 350b).

Based on a plan view, the size and shape of the first blade 348a, the second blade 348b, and portions of the first actuator 350a and the second actuator 350b on which they are integrally formed (or mounted) may correspond to the size and shape of the reservoir outlets in the insert 342.

Additionally, as shown in FIG. 27, the first activation pin 314a and the second activation pin 314b may include projecting edges (e.g., curved inner lips which face each other) configured to push the two punctured sections of the seal 344 into the reservoir as the first blade 348a and the second blade 348b advance into the reservoir. In a non-limiting embodiment, when the first activation pin 314a and the second activation pin 314b are fully inserted into the non-nicotine pod assembly 300, the two flaps (from the two punctured sections of the seal 344) may be between the curved sidewalls of the reservoir outlets of the insert 342 and the corresponding curvatures of the projecting edges of the first activation pin 314a and the second activation pin 314b. As a result, the likelihood of the two punctured openings in the seal 344 becoming obstructed (by the two flaps from the two punctured sections) may be reduced or prevented. Furthermore, the first activation pin 314a and the second activation pin 314b may be configured to guide the non-nicotine pre-vapor formulation from the reservoir toward the absorbent material 346 within the top hat holder 345.

The lower portion (e.g., distal portion) of each of the first actuator 350a and the second actuator 350b is configured to extend through a bottom section (e.g., upstream end) of the second housing section 308. This rod-like portion of each of the first actuator 350a and the second actuator 350b may also be referred to as the shaft. The first O-ring 352a and the second O-ring 352b may be seated in annular grooves in the respective shafts of the first actuator 350a and the second actuator 350b. The first O-ring 352a and the second O-ring 352b are configured to engage with the shafts of the first actuator 350a and the second actuator 350b as well as the inner surfaces of the corresponding openings in the second housing section 308 in order to provide a fluid-tight seal. As a result, when the first activation pin 314a and the second activation pin 314b are pushed inward to activate the non-nicotine pod assembly 300, the first O-ring 352a and the second O-ring 352b may move together with the respective shafts of the first actuator 350a and the second actuator 350b within the corresponding openings in the second housing section 308 while maintaining their respective seals, thereby helping to reduce or prevent leakage of the non-nicotine pre-vapor formulation through the openings in the second housing section 308 for the first activation pin 314a and the second activation pin 314b. The first O-ring 352a and the second O-ring 352b may be formed of silicone.

The perforator for the non-nicotine pod assembly 300 may include a notch configured to engage with a clip to preclude a premature actuation of the perforator. For instance, the shafts of the first activation pin 314a and the second activation pin 314b may define a first notch 351a and a second notch 351b, respectively, configured to engage with such a clip. In an example embodiment, the clip may be a planar structure defining a first slot and a second slot configured to engage with the first notch 351a and a second notch 351b, respectively. When engaged with the shafts of the first activation pin 314a and the second activation pin 314b (via the first notch 351a and a second notch 351b, respectively), the clip may be adjacent to the second housing section 308, thereby preventing the first activation pin 314a and/or the second activation pin 314b from being inadvertently pushed into the non-nicotine pod assembly 300. As a result, the first activation pin 314a and the second activation pin 314b may be adequately restrained (e.g., during shipping and/or handling) to reduce or prevent the possibility of their premature actuation. The clip may be removed (e.g., by an adult vaper) at an appropriate time when the non-nicotine pod assembly 300 is to be activated.

Figure 28:
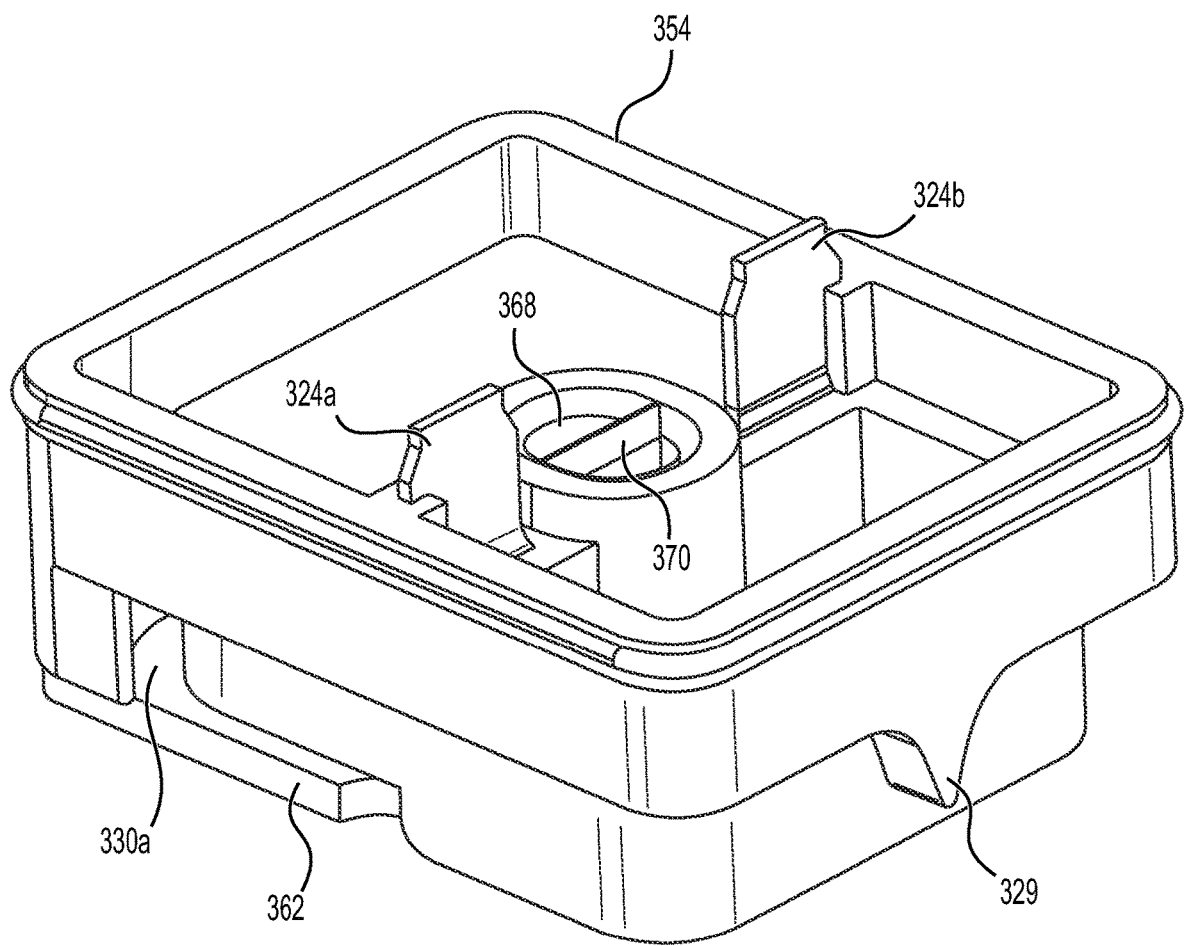
FIG. 28 is a perspective view of the connector module of FIG. 22 without the wick and heater.
Figure 29:
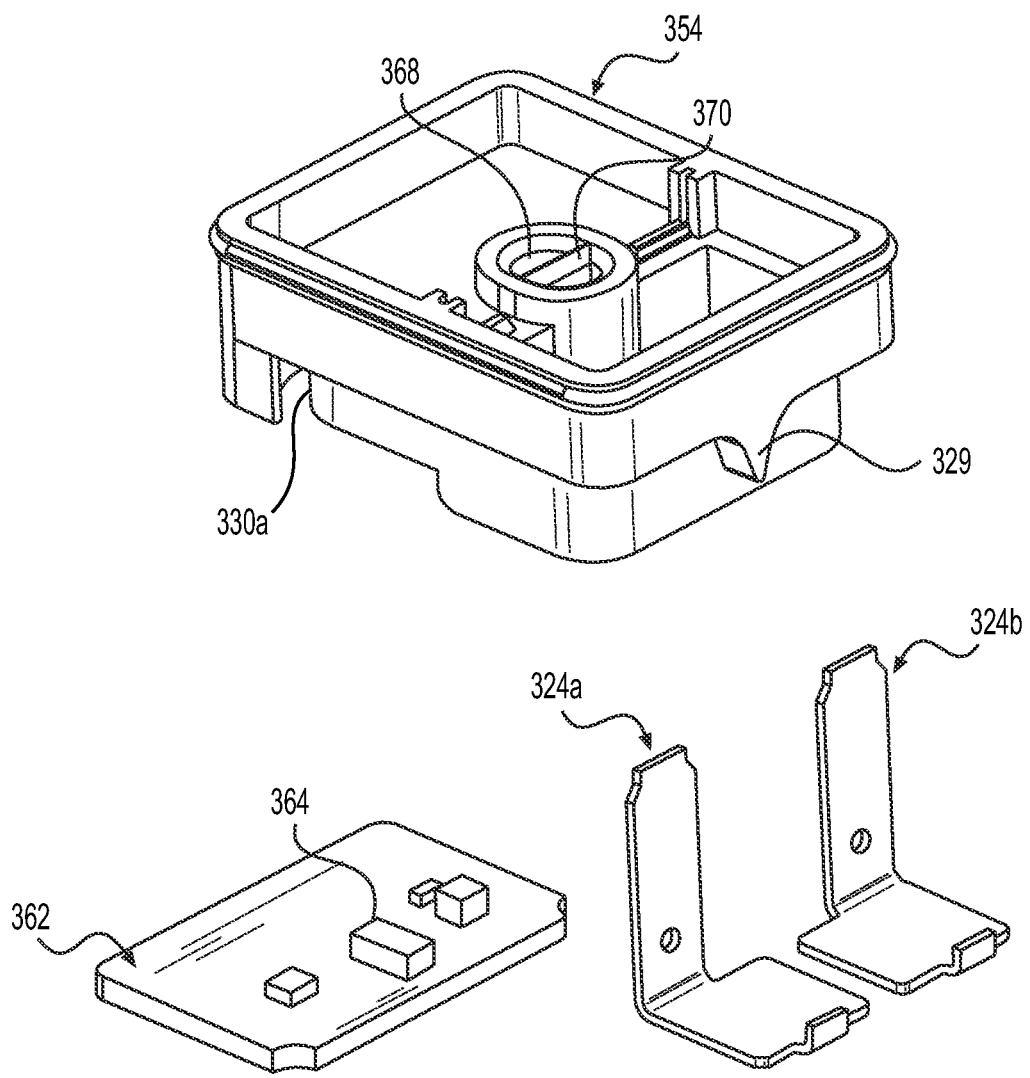
FIG. 29 is an exploded view of the connector module of FIG. 28.
Figure 30:
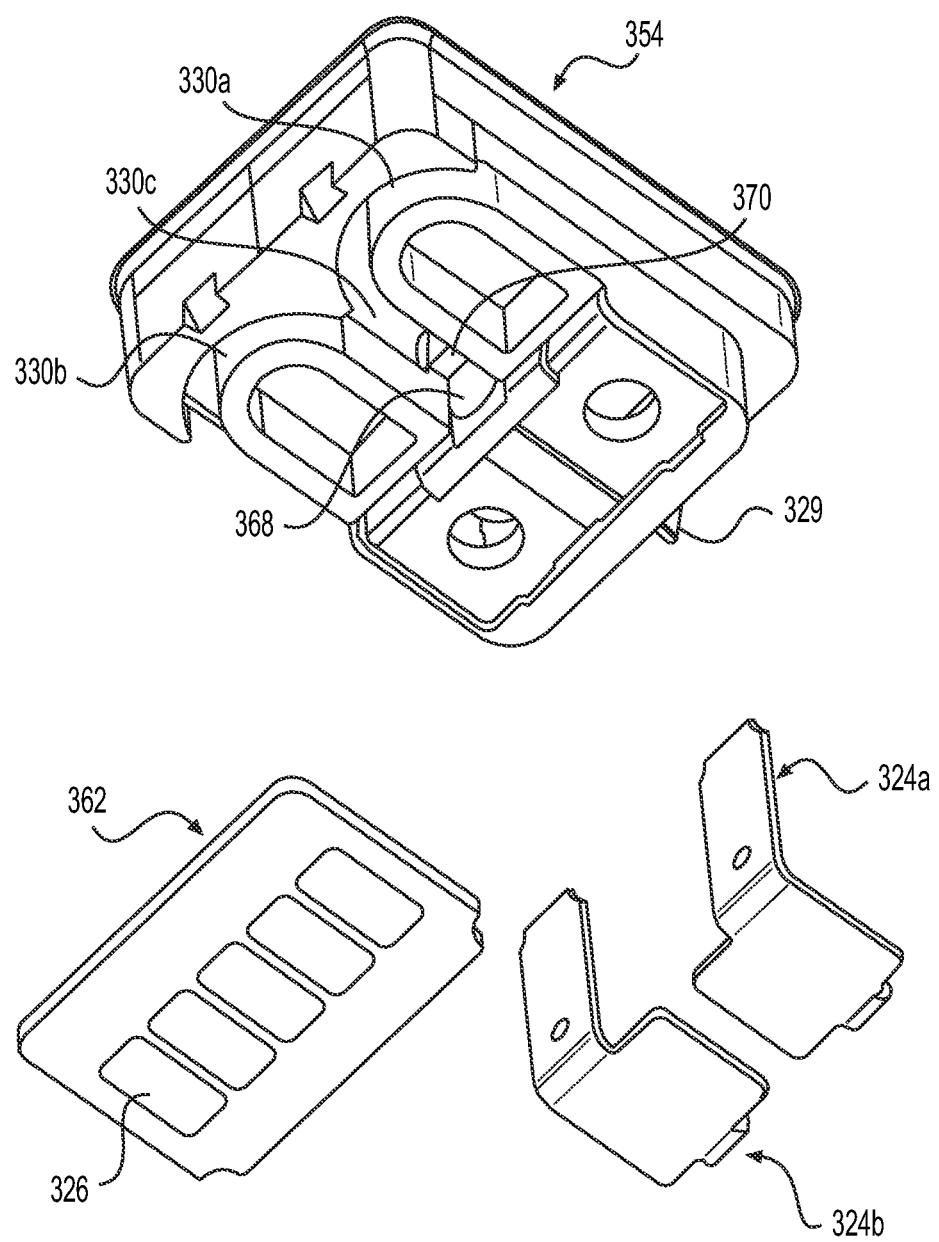
FIG. 30 is another exploded view of the connector module of FIG. 28.

FIG. 28 is a perspective view of the connector module of FIG. 22 without the wick and heater. FIG. 29 is an exploded view of the connector module of FIG. 28. FIG. 30 is another exploded view of the connector module of FIG. 28. Referring to FIGS. 28-30, the module housing 354 forms the framework of the connector module 320. The module housing 354 defines, inter alia, the divider 329 and the flow path for the air drawn into the non-nicotine pod assembly 300. When assembled within the non-nicotine pod assembly 300, the downstream rim of the module housing 354 may be engaged with the upstream rim of the base portion 345a of the top hat holder 345 (e.g., FIG. 26). As a result, the heater 336 and the wick 338 (e.g., FIG. 22) may be enclosed (at least partially) by the module housing 354 and the top hat holder 345. In addition, the internal space defined by the module housing 354 and the top hat holder 345 when assembled (within which the heater 336 and the wick 338 are disposed) may be regarded as a heating chamber. The heating chamber is in fluidic communication with the flow path in the upstream side of the module housing 354 via a module outlet 368.

As noted supra, the flow path for the air drawn into the non-nicotine pod assembly 300 includes a first diverged portion, a second diverged portion, and a converged portion defined by the module housing 354. In an example embodiment, the first diverged portion and the second diverged portion are symmetrical portions bisected by an axis corresponding to the converged portion of the flow path. For instance, as shown in FIG. 30, the first diverged portion, the second diverged portion, and the converged portion may include a first curved path 330a, a second curved path 330b, and a converged path 330c, respectively. The first curved path 330a and the second curved path 330b may be substantially U-shaped paths, while the converged path 330c may be substantially a linear path. Based on an axis corresponding to the converged path 330c and aligned with a crest of the divider 329, the first diverged portion of the flow path may be a mirror image of the second diverged portion of the flow path. During vaping, the air drawn through the pod inlet 322 may be split by the divider 329 and initially flow in opposite directions away from the divider 329, followed by a subsequent flow in parallel before each air stream makes a U-turn (via the first curved path 330a and the second curved path 330b) and convenes (via the converged path 330c) for a combined flow that travels back toward the divider 329 prior to passing through the module outlet 368 to the heating chamber. The heater 336 and the wick 338 may be positioned such that both sides are exposed substantially equally to the flow of air passing through the module outlet 368. During vaping, the non-nicotine vapor generated is entrained by the flow of air traveling through the heating chamber to the vapor channel 316.

A partition 370 may be disposed within the module outlet 368 to split the flow of air entering the heating chamber. The heater 336 and the wick 338 (e.g., FIG. 22) are downstream from the module outlet 368 and may be oriented so as to be aligned with the partition 370. As a result of the partition 370, the flow of air may be split relatively equally such that a first flow passes along a first side of the heater 336 (and the wick 338) while a second flow passes along a second side of the heater 336 (and the wick 338). In an example embodiment, the magnitudes (e.g., velocity, volumetric flow rate, mass flow rate) of the first flow and the second flow may be within ±10% of each other. For instance, with regard to the air drawn into the heating chamber, 51% may be part of the first flow, while 49% may be part of the second flow, although it should be understood that variations within the above range may occur. In addition to reducing the flow imbalance through the heating chamber, the partition 370 may also be regarded as a flow straightener.

The partition 370 may be in a form of a bar that extends across (e.g., bisects) the module outlet 368. As for dimensions, the partition 370 may have a thickness of about 150-250 μm (e.g., 200 μm). The thickness of the partition 370 coincides with the extent to which the module outlet 368 is obstructed by the partition 370. Consequently, the thickness of the partition 370 and/or the size of the module outlet 368 may be adjusted to provide the desired resistance-to-draw (e.g., 25 mmH$_2$O) for the non-nicotine e-vaping device 500. In addition, the width of the partition 370 may be between 525-875 μm (e.g., 700 μm). The width may be such that the partition 370 extends along a majority or an entirety of the passage defined by the module outlet 368. Furthermore, assuming a circular cross-section for the module outlet 368, the length of the partition 370 may correspond to the diameter of the module outlet 368. Alternatively, in instances where the module outlet 368 has an elliptical cross-section, the length of the partition 370 may correspond to an axis (e.g., minor axis, major axis) of the module outlet 368.

As illustrated in FIGS. 29-30, each of the first power contact 324a and the second power contact 324b may include a contact face and a contact leg. The contact leg (which may have an elongated configuration) may be oriented orthogonally relative to the contact face (which may be square-shaped), although example embodiments are not limited thereto. The module housing 354 may define a pair of shallow depressions and a pair of apertures to facilitate the mounting of the first power contact 324a and the second power contact 324b. During assembly, the contact face of each of the first power contact 324a and the second power contact 324b may be seated in a corresponding one of the pair of shallow depressions so as to be substantially flush with the external face of the module housing 354 (e.g., FIG. 21). In addition, the contact leg of each of the first power contact 324a and the second power contact 324b may extend through a corresponding one of the pair of apertures so as to protrude from the downstream side of the module housing 354 (e.g., FIG. 28). The heater 336 can be subsequently connected to the contact leg of each of the first power contact 324a and the second power contact 324b.

The printed circuit board (PCB) 362 includes the plurality of data contacts 326 on its upstream side (e.g., FIG. 30) and various electronic components, including a sensor 364, on its downstream side (e.g., FIG. 29). The sensor 364 may be positioned on the printed circuit board (PCB) 362 such that the sensor 364 is within the converged path 330c defined by the module housing 354. In an example embodiment, the printed circuit board (PCB) 362 (and associated components secured thereto) is an independent structure that is initially inserted into the receiving cavity in the downstream side of the second housing section 308 such that the data contacts 326 are exposed by the data contact opening 327 of the second housing section 308. Afterwards, the module housing 354 (with the first power contact 324a, the second power contact 324b, the heater 336, and the wick 338 mounted thereon) may be inserted into the receiving cavity such that the first power contact 324a and the second power contact 324b are exposed by the first power contact opening 325a and the second power contact opening 325b, respectively, of the second housing section 308. Alternatively, to simplify the above two-step insertion process to a one-step insertion process, it should be understood that the printed circuit board (PCB) 362 (and associated components secured thereto) may be affixed to the module housing 354 (e.g., to form a single integrated structure) so as to cover the first curved path 330a, the second curved path 330b, the converged path 330c, and the module outlet 368.

As noted supra, the module outlet 368 may be a resistance-to-draw (RTD) port. In such a configuration, the resistance-to-draw for the non-nicotine e-vaping device 500 may be adjusted by changing the size of the module outlet 368 (rather than changing the size of the pod inlet 322). In an example embodiment, the size of the module outlet 368 may be selected such that the resistance-to-draw is between 20-100 mmH$_2$O (e.g., between 25-50 mmH$_2$O). For instance, a diameter of 1.0 mm for the module outlet 368 may result in a resistance-to-draw of 88.3 mmH$_2$O. In another instance, a diameter of 1.1 mm for the module outlet 368 may result in a resistance-to-draw of 73.6 mmH$_2$O. In another instance, a diameter of 1.2 mm for the module outlet 368 may result in a resistance-to-draw of 58.7 mmH$_2$O. In yet another instance, a diameter of 1.3 mm for the module outlet 368 may result in a resistance-to-draw of about 40-43 mmH$_2$O. Notably, the size of the module outlet 368, because of its internal arrangement, may be adjusted without affecting the external aesthetics of the non-nicotine pod assembly 300, thereby allowing for a more standardized product design for non-nicotine pod assemblies with various resistance-to-draw (RTD) while also reducing the likelihood of an inadvertent blockage of the incoming air.

The device body 100 and the non-nicotine pod assembly 300 as well as other aspects of the non-nicotine e-vaping device 500 may also be as described in U.S. application Ser. No. 16/696,189, titled "Non-nicotine Pod Assemblies And Non-nicotine E-vaping Devices", filed concurrently herewith, and in U.S. application Ser. No. 16/695,515, titled "Non-nicotine Pod Assemblies And Non-nicotine E-vaping Devices", filed concurrently herewith, the entire contents of each of which are incorporated herein by reference.

In an example embodiment, the non-nicotine pre-vapor formulation neither includes tobacco nor is derived from tobacco. A non-nicotine compound of the non-nicotine pre-vapor formulation may be part of, or included in a liquid or a partial-liquid that includes an extract, an oil, an alcohol, a tincture, a suspension, a dispersion, a colloid, a general non-neutral (slightly acidic or slightly basic) solution, or combinations thereof. During the preparation of the non-nicotine pre-vapor formulation, the non-nicotine compound may be infused into, comingled, or otherwise combined with the other ingredients of the non-nicotine pre-vapor formulation.

In an example embodiment, the non-nicotine compound undergoes a slow, natural decarboxylation process over an extended duration of time at relatively low temperatures, including at or below room temperature (e.g., 72° F.). In addition, the non-nicotine compound may undergo a significantly elevated decarboxylation process (e.g., 50% decarboxylation or greater) if exposed to elevated temperatures, especially in the range of about 175° F. or greater over a period of time (minutes or hours) at a relatively low pressure such as 1 atmosphere. Higher temperatures of about 240° F. or greater can cause a rapid or instantaneous decarboxylation to occur at a relatively high decarboxylation rate, although further elevated temperatures can cause a degradation of some or all of the chemical properties of the non-nicotine compound(s).

In an example embodiment, the non-nicotine compound may be from a medicinal plant (e.g., a naturally-occurring constituent of a plant that provides a medically-accepted therapeutic effect). The medicinal plant may be a *Cannabis* plant, and the constituent may be at least one *Cannabis*-derived constituent. Cannabinoids (e.g., phytocannabinoids) and terpenes are examples of *Cannabis*-derived constituents. Cannabinoids interact with receptors in the body to produce a wide range of effects. As a result, cannabinoids have been used for a variety of medicinal purposes. *Cannabis*-derived materials may include the leaf and/or flower material from one or more species of *Cannabis* plants, or extracts from the one or more species of *Cannabis* plants. For instance, the one or more species of *Cannabis* plants may include *Cannabis sativa, Cannabis indica*, and *Cannabis ruderalis*. In some example embodiments, the non-nicotine pre-vapor formulation includes a mixture of *Cannabis* and/or *Cannabis*-derived constituents that are, or are derived from, 60-80% (70%) *Cannabis sativa* and 20-40% (e.g., 30%) *Cannabis indica.*

Non-limiting examples of *Cannabis*-derived cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from the heater may cause decarboxylation to convert tetrahydrocannabinolic acid (THCA) in the non-nicotine pre-vapor formulation to tetrahydrocannabinol (THC), and/or to convert cannabidiolic acid (CBDA) in the non-nicotine pre-vapor formulation to cannabidiol (CBD).

In instances where both tetrahydrocannabinolic acid (THCA) and tetrahydrocannabinol (THC) are present in the non-nicotine pre-vapor formulation, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC), via the decarboxylation process, during the heating of the non-nicotine pre-vapor formulation for purposes of vaporization. Similarly, in instances where both cannabidiolic acid (CBDA) and cannabidiol (CBD) are present in the non-nicotine pre-vapor formulation, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD), via the decarboxylation process, during the heating of the non-nicotine pre-vapor formulation for purposes of vaporization.

The non-nicotine pre-vapor formulation may contain the non-nicotine compound that provides the medically-accepted therapeutic effect (e.g., treatment of pain, nausea, epilepsy, psychiatric disorders). Details on methods of treatment may be found in U.S. application Ser. No. 15/845,501, filed Dec. 18, 2017, titled "VAPORIZING DEVICES AND METHODS FOR DELIVERING A COMPOUND USING THE SAME," the disclosure of which is incorporated herein in its entirety by reference.

In an example embodiment, at least one flavorant is present in an amount ranging from about 0.2% to about 15% by weight (e.g., about 1% to 12%, about 2% to 10%, or about 5% to 8%) based on a total weight of the non-nicotine pre-vapor formulation. The at least one flavorant may be at least one of a natural flavorant, an artificial flavorant, or a combination of a natural flavorant and an artificial flavorant. The at least one flavorant may include volatile *Cannabis* flavor compounds (flavonoids) or other flavor compounds instead of, or in addition to, the *Cannabis* flavor compounds. For instance, the at least one flavorant may include menthol, wintergreen, peppermint, cinnamon, clove, combinations thereof, and/or extracts thereof. In addition, flavorants may be included to provide other herb flavors, fruit flavors, nut flavors, liquor flavors, roasted flavors, minty flavors, savory flavors, combinations thereof, and any other desired flavors.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A non-nicotine pod assembly for a non-nicotine e-vaping device, comprising:
    a first section defining a pod outlet and configured to hold a non-nicotine pre-vapor formulation; and
    a second section connected to the first section, the second section defining a pod inlet and configured to heat the non-nicotine pre-vapor formulation, the pod inlet in fluidic communication with the pod outlet via a flow path, the flow path including a first diverged portion, a second diverged portion, and a converged portion.

2. The non-nicotine pod assembly of claim 1, wherein the first section is configured to hermetically seal the non-nicotine pre-vapor formulation until an activation of the non-nicotine pod assembly.

3. The non-nicotine pod assembly of claim 2, wherein the second section includes a perforator configured to release the non-nicotine pre-vapor formulation from the first section during the activation of the non-nicotine pod assembly.

4. The non-nicotine pod assembly of claim 3, wherein the perforator includes a notch configured to engage with a clip to preclude a premature actuation of the perforator.

5. The non-nicotine pod assembly of claim 1, wherein the pod inlet is upstream from the first diverged portion and the second diverged portion of the flow path.

6. The non-nicotine pod assembly of claim 1, wherein the converged portion of the flow path is downstream from the first diverged portion and the second diverged portion.

7. The non-nicotine pod assembly of claim 1, wherein the first diverged portion and the second diverged portion convene to form the converged portion of the flow path.

8. The non-nicotine pod assembly of claim 1, wherein the second section includes a divider configured to direct an incoming air flow into the first diverged portion and the second diverged portion of the flow path.

9. The non-nicotine pod assembly of claim 8, wherein the divider is wedge-shaped and configured to split the incoming air flow into opposite directions.

10. The non-nicotine pod assembly of claim 1, wherein the first diverged portion includes a first curved segment.

11. The non-nicotine pod assembly of claim 1, wherein the second diverged portion includes a second curved segment.

12. The non-nicotine pod assembly of claim 1, wherein the first diverged portion and the second diverged portion are symmetrical portions bisected by an axis corresponding to the converged portion of the flow path.

13. The non-nicotine pod assembly of claim 1, wherein the second section includes a heater and a wick downstream from the converged portion of the flow path.

14. The non-nicotine pod assembly of claim 13, wherein the heater includes a folded heating element configured to grip the wick.

15. The non-nicotine pod assembly of claim 14, wherein the folded heating element includes at least one prong configured to protrude into the wick.

16. The non-nicotine pod assembly of claim 13, wherein the second section further includes an absorbent material seated within a holder, the absorbent material being downstream from and in fluidic communication with the wick.

17. The non-nicotine pod assembly of claim 16, wherein the absorbent material is configured to receive the non-nicotine pre-vapor formulation from the first section, and the wick is configured to transfer the non-nicotine pre-vapor formulation from the absorbent material to the heater.

18. The non-nicotine pod assembly of claim 16, wherein the absorbent material has an annular form, and the wick has a planar form.

19. The non-nicotine pod assembly of claim 16, wherein the holder includes a base portion and a cylindrical portion.

20. A device body for a non-nicotine e-vaping device, comprising:

a device housing defining a through hole configured to receive a non-nicotine pod assembly, the through hole including an upstream sidewall and a downstream sidewall, the upstream sidewall including at least one upstream protrusion, the downstream sidewall including at least one downstream protrusion, the at least one downstream protrusion being retractable relative to adjacent surfaces of the downstream sidewall and configured to engage with at least one downstream recess of the non-nicotine pod assembly to retain the non-nicotine pod assembly within the through hole.

21. A non-nicotine e-vaping device, comprising:

a non-nicotine pod assembly including a first section and a second section, the first section configured to hold a non-nicotine pre-vapor formulation, the second section configured to diverge and converge an air flow into the non-nicotine pod assembly prior to a passage of the air flow through the first section; and a device body defining a through hole configured to receive the non-nicotine pod assembly such that a pod inlet for the air flow is exposed when the non-nicotine pod assembly is seated within the through hole.

* * * * *